(12) United States Patent
Liberator et al.

(10) Patent No.: US 7,390,892 B2
(45) Date of Patent: Jun. 24, 2008

(54) **NUCLEIC ACIDS ENCODING NOVEL CYCLIC GMP DEPENDENT PROTEIN KINASES FROM *ELMERIA MAXIMA***

(75) Inventors: Paul Liberator, Holmdel, NJ (US); Dennis Schmatz, Cranford, NJ (US); Anne Gurnett, New York, NY (US); Carmen Diaz, New York, NY (US)

(73) Assignee: Merial Limited, Duluth, GA (US)

( * ) Notice: Subject to any disclaimer, the term of this patent is extended or adjusted under 35 U.S.C. 154(b) by 23 days.

(21) Appl. No.: 10/499,554

(22) PCT Filed: Dec. 18, 2002

(86) PCT No.: PCT/US02/40527

§ 371 (c)(1), (2), (4) Date: Jan. 31, 2005

(87) PCT Pub. No.: WO03/054157

PCT Pub. Date: Jul. 3, 2003

(65) Prior Publication Data

US 2005/0147628 A1    Jul. 7, 2005

Related U.S. Application Data

(60) Provisional application No. 60/342,816, filed on Dec. 20, 2001.

(51) Int. Cl.
*C07H 21/02* (2006.01)
*C07H 21/04* (2006.01)
*C12N 15/00* (2006.01)
*C12P 1/00* (2006.01)

(52) U.S. Cl. ............ 536/23.2; 536/23.1; 536/23.7; 435/320.1; 435/41

(58) Field of Classification Search .............. None
See application file for complete search history.

(56) References Cited

U.S. PATENT DOCUMENTS 5,792,778 A    8/1998   de Laszlo et al.
6,555,358 B1   4/2003   Gurnett et al.

FOREIGN PATENT DOCUMENTS

WO        WO 00 61781        10/2000

OTHER PUBLICATIONS

Greenspan et al. (Nature Biotechnology 7: 936-937, 1999).*
Bowie et al (Science, 1990, 247:1306-1310).*
Overbeek (1994, "Factors affecting transgenic animal production," Transgenic animal technology, pp. 96-98).*
Wall, 1996 Theriogenology, vol. 45, pp. 57-68.*
Kappell, 1992, Current Opinions in Biotechnology, vol. 3, pp. 548-553.*
Cameron, 1997, Molec. Biol. 7, pp. 253-265, specifically p. 256, col. 1-2, bridge, parag.*
(Niemann, 1997, Transg. Res. 7, pp. 73-75, specifically p. 73, col. 2, parag. 2, line 12 to p. 73, col. 1, line 4.*
Hammer (1990, Cell, vol. 63, 1099-1112).*
Taurog, 1988, Jour. Immunol., vol. 141, pp. 4020-4023).*
Williams, R. B., "A compartmentalized model for the estimation of the cost of coccidiosis to the world's poultry production industry", International Journal of Parasitology, 29:1209-1229 (1999).
Stephan, B. et al., "Studies of resistance to anticoccidials in *Eimeria* field isolates and pure *Eimeria* strains", Veterinary Parasitology, 69:19-29 (1997).
Langreth & Peterson, "Pathogenicity, Stability, and Immunogenicity of a Knobless Clone of *Plasmodium falciparum* in Colombian Owl Monkeys", Infection and Immunity, 47(3):760-766 (1985).
Baucage & Carruthers, "Deoxynucleoside Phosphoramidites-A New Class of Key Intermediates for Deoxypolynucleotide Synthesis", Tetrahedron Letters, 22(20):1859-1862 (1981).
DeLuca, Dominick, Antibody as a Tool, "Immunofluorescence Analysis", Eds.Marchalonis & Warr, John Wiley & Sons, Ltd., 189-231 (1982).
Denhardt, David T., "A Membrane-Filter Technique for the Detection of Complementary DNA", Biochemical and Biophysical Research Communications, 23(5):641-646 (1966).
Frohman, et al., "Rapid production of full-length cDNAs from rare transcripts: Amplification using a single gene-specific oligonucleotide primer", Proc. Natl. Acad. Sci., 85:8998-9002 (1988).
Sambrook et al., "Molecular Cloning: A Laboratory Manual"; Cold Spring Harbor Laboratory, Cold Spring Harbor, NY (1989).
Wallace et al., "The use of synthetic oligonucleotides as hybridization probes. II. Hybridization of oligonuleotides of mixed sequence of rabbit β-globin DNA", Nucleic Acids Research, 9:879-894 (1981).
Weintraub, Harold M., "Antisense RNA and DNA", Scientific American, 262:40-46 (1990).
Marcus-Sakura, Carol J., "Techniques for Using Antisense Oligodeoxyribonucleotides to Study Gene Expression", Analytical Biochemistry, 172:289-295 (1988).
Kohler & Milstein, "Continuous cultures of fused cells secreting antibody of predefined specificity", Nature, 256:495-497 (1975).

(Continued)

*Primary Examiner*—Robert A. Zeman
(74) *Attorney, Agent, or Firm*—Judy Jarecki-Black; Merial Limited; Thomas Kowalski, Esq.

(57) ABSTRACT

The present invention relates to novel protozoal cyclic GMP dependent protein kinases and genes encoding same that have been isolated from *Eimeria maxima* and *Plasmodium falciparum*. Nucleic acid molecules having sequences that encode such proteins as well as antibodies raised against such proteins are also disclosed. These enzymes may be used in screening assays to identify potential antiprotozoal agents. As well, methods to obtain such nucleic acid molecules, proteins, antibodies and inhibitor are also provided as are therapeutic compositions comprising such nucleic acid molecules, proteins, antibodies and inhibitors as well as their use to protect animals from disease caused by parasites such as *Eimeria maxima* and *Plasmodium falciparum*.

7 Claims, 1 Drawing Sheet

OTHER PUBLICATIONS

MacPherson, Ian; "Soft Agar Techniques"; Tissue Culture Methods and Applications; Kruse and Paterson, Eds., Academic Press, 276-280 (1973).

Soldati & Boothroyd, "Transient Transfection and Expression in the Obligage Intracellular Parasite *Toxoplasma gondii*", Science, 260:349-352 (1993).

Roos et al., "Molecular Tools for Genetic Dissection of the Protozoan Parasite *Toxoplasma gondii*", Methods in Cell Biology, 45:27-63 (1994).

Black et al., "Restriction enzyme-mediated integration elevates transformations frequency and enables co-transfection of *Toxoplasma gondii*", Molecular and Biochemical Parasitology, 74:55-63 (1995).

Brown et al., "Protein Measurement Using Bicinchoninic Acid: Elimination of Interfering Substances", Analytical Biochemistry, 180:136-139 (1989).

Schmatz et al., "*Eimeria tenella*: Parasite-Specific Incorporation 3H-Uracil as a Quantitative Measure of Intracellular Development", J. Protozoology, 33:109-114 (1986).

Tager & Jensen, "Human Malaria Parasites in Continuous Culture", Science, 193:673-675 (1976).

Lambros & Vanderberg, Synchronization of Plasmodium Falciparum Erythrocytic Stages in Culture, J. Parasitology, 65(3):418-420 (1979).

Rivadeneira et al., "Separation and Concentration of Schizonts of *Plasmodium falciparum* by Percoll Gradients", J. Protozoology, 30:367-370 (1983).

Deng et al., "A novel cyclic GMP-dependent protein kinase is expressed in the ring stage of the *Plasmodium falciparum* life cycle", Molecular Microbiology, 44(5):1141-1151 (2002).

Gurnett et al., "Purification and Molecular Characterization of cGMP-dependent Protein Kinase from Apicomplexan Parasites", Journal of Biological Chemistry, 277(18): 15913-15922 (2002).

Database EMBL: Accession No. BM168332.

Donald, Robert G. K. et al., "Molecular characterization of a coccidian parasite cGMP dependent protein kinase", Molecular and Biochemical Parasitology, 120(2):165-175 (2002).

* cited by examiner

NUCLEIC ACIDS ENCODING NOVEL CYCLIC GMP DEPENDENT PROTEIN KINASES FROM *ELMERIA MAXIMA*

CROSS-REFERENCE TO RELATED APPLICATIONS

This application claims the benefit of U.S. Provisional Application No. 60/342,816, filed Dec. 20, 2001, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

The present invention relates to novel parasite cGMP dependent protein kinase (PKG) encoding genes, proteins encoded by such genes, and antibodies raised against such proteins. Particular PKG's of the present invention include those encoded by the novel nucleic acid molecules detailed herein. The present invention also includes therapeutic compositions comprising such nucleic acid molecules, proteins, antibodies and inhibitors, as well as their use to protect animals and man from disease caused by parasites, such as *Eimeria maxima* and *Plasmodium falciparum* respectively. Methods for identifying potential antiprotozoal agents using the novel kinases of the invention, as well as a method for treating protozoal infections are also provided.

BACKGROUND OF THE INVENTION

Parasitic protozoa are responsible for a wide variety of infections in man and animals, many of which are life threatening to the host. For example, members of the phylum Apicomplexa (formerly called Sporozoa) comprise a large and diverse group of pathogenic protozoa that are intracellular parasites which vary tremendously in virulence depending upon the species with which the host is infected. Some species cause diseases that result in mild symptoms that might go unnoticed (i.e., mild diarrhea) and eventually disappear, while other species cause highly virulent infections that are rapidly fatal. In animal husbandry, many of these diseases can cause considerable economic loss to the owners, as many such diseases can cause effects to the animals which may not be apparent until the animal is prepared for market. For example, poultry are generally marketed within weeks after hatching and this short time period does not permit the animals sufficient time to recover from a chronic infection prior to market if not treated in time.

A protozoal infection of great economic importance in the food industry is coccidiosis, a widespread disease of domesticated animals caused by protozoa of the genus *Eimeria*. Some of the most significant of *Eimeria* species are those in poultry, namely *E. tenella, E. acervulina, E. necatrix, E. brunetti, E. praecox, E. mitis* and *E. maxima*. The disease is responsible for high levels of morbidity and mortality and can result in extreme economic losses. Accordingly, there exists a continued need to identify new and effective anti-protozoal drugs.

While coccidiosis occurs in several domesticated and wild animal species, such as cattle, sheep, pigs and rabbits, the disease is especially important in poultry, in particular chickens. See Williams, R. B., A compartmentalized model for the estimation of the cost of coccidiosis to the world's poultry production industry, *Int. J. Parasitology,* 29: 1209-1229 (1999).

The disease is caused by the replication within the intestine of the asexual and/or sexual stages of seven species of *Eimeria* (usually several species occur concurrently) and although clinical disease in intensively reared poultry is now relatively uncommon, sub clinical infections are the norm. The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have their market value substantially reduced as a result of the infection. Of the seven species of *Eimeria*, the most pathogenic species are *E. necatrix* and *E. tenella*, followed by *E. maxima*. The least pathogenic species is *E. praecox*.

The total cost of coccidial infections in the US runs in the hundreds of millions of dollars. In the UK alone, the total cost, corresponding to about 780 million broilers, has been estimated to be at least £42 m per annum, of which 74% is due to sub-clinical effects on weight gain and feed conversion and 24% is the cost of prophylaxis and therapy of commercial birds. See Williams, supra;

Presently, poultry flocks are protected against coccidiosis by either immunization or the use of anti-coccidial chemotherapeutic agents with the most commonly utilized method for controlling coccidial infections being the use of anticoccidial agents. The most successful anticoccidials have been the polyether ionophores, a class of antibiotics of complex structure, which continues to be the industry standard since its introduction nearly thirty years ago. While many such ionophores exhibit anti-coccidial activity, the relative degree of activity varies from one agent to another. As well, the use of ionophores for controlling coccidiosis in animals requires that the agent be continuously administered to the animal typically by being mixed with the feed used for the entire growth period. Reports of resistance development due to the extended and constant chemotherapeutic pressure exerted by this class of compounds are not uncommon. See Stephen, B. et al., *Vet. Parasitol.,* 69: 19-29 (1997) and Daugschies et al., *Vet. Parasitol.,* 76: 163-171(1998). As such, there is a dire need to develop antiprotozoal compounds that are not attended by the above referenced drawbacks.

Probably the most well-studied acomplexicans are species of *Plasmodium*, an obligate intracellular parasite, which is the causative agent for malaria. Malaria remains a significant health threat to humans despite massive international attempts to eradicate the disease. There are four species of *Plasmodium* which infect humans. *P. falciparum, P. vivax, P. malariae*, and *P. ovale.*

Alone among the malaria species which infect humans, *Plasmodium falciparum* causes the erythrocytes, which it invades to sequester in the deep vascular beds of various tissues. Sequestration allows the parasite to develop in a microenvironment of low oxygen tension and to evade splenic immune surveillance (Langreth and Peterson (1985) Infect. Immun. 47: 760-766). *P. falciparum* is the most virulent species of malaria since it can cause the death of the host as a result of: cerebral malaria, pulmonary or renal failure.

More than ten years ago an urgent need for drugs against malaria was identified. The antibiotics currently in use for the treatment and prophylaxis of malaria (including the tetracyclines and clindamycin) have little action on pre-erythrocytic stages and act slowly on blood stages, but are used for treatment of drug resistant strains because of their safety rather than their efficacy. Furthermore, the rapid spread of resistance to chloroquine has heightened the need for ready availability of relatively low cost prophylactic and therapeutic anti-malarial drugs. Owing to the devastating consequences of the disease, and the potential for therapeutic intervention, researchers have long sought to identify the parasite protein(s) responsible for the devastating effects attending *Plasmodium falciparum* infection.

Although discovered in 1963, the importance of the cyclic nucleotide cofactor cGMP in many cellular and physiological processes was first described in the late 1970s (Lincoln and Cornwell, 1993; Baumner and Nawrath, 1995; Moro et al., 1996; Vaandrager and de Jonge, 1996). cGMP is generated by guanylate cyclase (GC) and degraded by specific cyclic nucleotide phosphodiesterases (PDE). It exerts its intracellular effects by interacting with a group of intracellular proteins known as intracellular cGMP receptor proteins (Lincoln and Cornwell, 1993), which include cGMP-dependent protein kinases (PKGs), cGMP-dependent phosphodiesterases (PDEs), and cGMP-gated ion channels.

It is believed that the binding and activation of cGMP-dependent protein kinase (PKG) is responsible for most of the intracellular actions of cGMP. PKGs are known to control many cellular processes in higher animals. Although expressed in many cell types, these serine/threonine protein kinases are found at high levels in mammalian lung, cerebellum, platelets, and SMCs (Francis and Corbin, 1994). cGMP dependent protein kinases (PKG) catalyze the phosphorylation of specific protein substrates. In the absence of cGMP the activity of these enzymes is very low.

The canonical phosphorylation site for PKG substrates (Arg-Arg-X-Ser) is the same described for cAMP-dependent protein kinases (PKA, Vaandrager and de Jonge, 1996). In mammalian cells there are two types of PKG, a soluble (PKG1) and a membrane bound form (PKG2). (Vaandrager and de Jonge, 1996). Multiple splice variants of the soluble protein have been identified. Type I -PKG1 has two isoforms (type I-α and type I-β), while type If is less common and expressed only in intestinal epithelial cells (Lincoln and Cornwell, 1993), kidney, and brain (Vaandrager and de Jonge, 1996).

The present invention overcomes previous shortcomings in developing effective treatments of various types of parasitic infections by providing the nucleotide sequence of the gene encoding *Eimeria maxima* PKG and *Plasmodium falciparum* PKG respectively, the novel protein kinases encoded by each of the nucleic acid molecules, and the use of the proteins as chemotherapeutic target(s). Therapeutics identified via use of the novel nucleic acids as well as the herein disclosed assays are likewise contemplated by the present invention.

SUMMARY OF THE INVENTION

The present invention rests with the discovery of two novel cGMP dependent protein kinases from the parasitic protozoa *Eimeria maxima* and *Plasmodium falciparum*.

Accordingly, disclosed herein is a novel protozoal cGMP dependent protein kinases (PKG) isolated from Eimeria maxima comprising the amino acid sequence of SEQ ID NO:2. The polynucleotide sequence encoding this polypeptide is depicted in of SEQ ID NO:1.

In another embodiment, the invention provides a substantially pure PKG of Plasmodium falciparum comprising the amino acid sequence of SEQ ID NO:4. The nucleotide sequence encoding the novel PKG is depicted in SEQ ID NO:3.

In another aspect the present invention provides a method for identifying compounds having antiprotozoal activity comprising:
(a) contacting protozoal PKG with, (i) a known amount of a labeled compound that interacts with a PKG and, (ii) a known dilution of a test compound or a natural product extract; and
(b) quantitating the percent inhibition of interaction of said labeled compound induced by said test compound.

In another aspect the present invention provides a method for identifying compounds having antiprotozoal activity comprising:
(a) contacting an intact host or protozoal cell with a test compound or a natural product extract;
(b) disrupting said cell to obtain a biochemical fraction possessing PKG catalytic activity; and
(c) determining the level of PKG activity in said biochemical fraction.

The methods of the invention provides a facile and specific assay to screen compounds as potential antiprotozoal drugs. Agents identified as a result thereof are also within the scope of the invention.

Accordingly, an embodiment of the invention provides evidence that a known compound, L-167645, inhibits the growth of parasites containing the herein disclosed PKG's, both in vitro and in vivo.

One such agent that shows promise as an antiprotozoal agent that inhibits cGMP-dependent protein kinase is a known compound exemplified by 4-[2-(4-fluorophenyl)-5-(1-methylpiperidine4-yl)-1H-pyrrol-3-yl]pyridine (L-167645). The inventors have shown herein that this compound is effective in inhibiting parasitic growth as exemplified in an in in vitro tissue culture based assays with *P. falciparum* and *C. parvum*. The inventors also show that growth of *P. falciparum* and *E. maxima* in vivo can be inhibited by oral administration of the compound to infected mice and chickens, respectively.

DETAILED DESCRIPTION OF THE INVENTION

Figure 1:
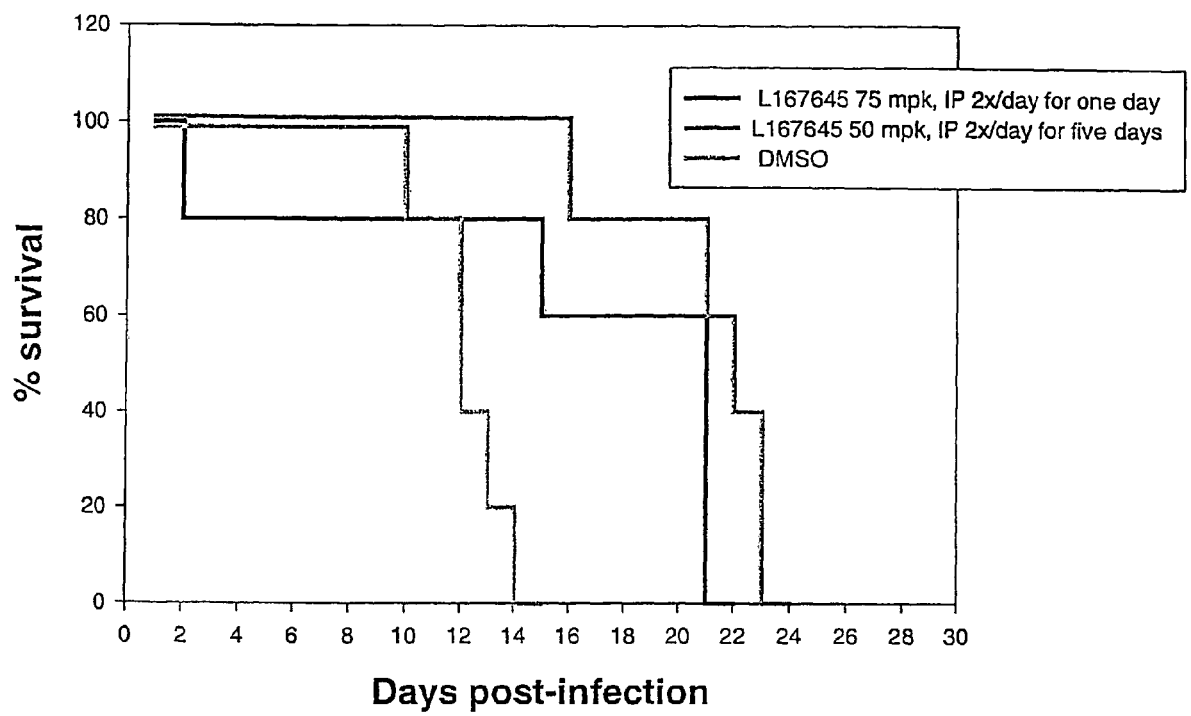
FIG. 1 depicts the results of an experiment demonstrating the efficacy of compound L-167645 in inhibiting protozoal infection. Data depicts the survival rate of Plasmodium-infected mice treated with L-167645.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described.

All publications mentioned herein are incorporated herein by reference for the purpose of describing and disclosing the methodologies, vectors etc which are reported in the publications that might be used in connection with the invention. Nothing herein is to be construed as an admission that the invention is not entitled to antedate such disclosure by virtue of prior invention.

In the description that follows, a number of terms used in the field of recombinant DNA technology are extensively utilized. In order to provide a clearer and consistent understanding of the specification and claims, including the scope to be given such terms, the following definitions are provided.

A "gene" refers to a nucleic acid molecule whose nucleotide sequence codes for a polypeptide molecule. Genes may be uninterrupted sequences of nucleotides or they may include such intervening segments as introns, promoter regions, splicing sites and repetitive sequences. A gene can be either RNA or DNA. A preferred gene is one that encodes the invention receptor protein.

The term "nucleic acid" or "nucleic acid molecule" is intended for ribonucleic acid (RNA) or deoxyribonucleic acid (DNA), probes, oligonucleotides, fragment or portions thereof, and primers. DNA can be either complementary DNA (cDNA) or genomic DNA, e.g. a gene encoding the invention receptor protein. Nucleic acid refers to DNA, RNA or cDNA.

Unless otherwise indicated, a nucleotide defines a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Each "nucleotide sequence" set forth herein is presented as a sequence of deoxyribonucleotides (abbreviated A, G, C and T). However, by "nucleotide sequence" of a nucleic acid molecule is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways described herein that the DNAs, RNAs, polypeptides or proteins as they naturally occur are not.

Similarly, as used herein, "recombinant" as a modifier of DNA, RNA, polypeptides or proteins means that the DNA, RNA, polypeptides or proteins so designated have been prepared by the efforts of human beings, e.g., by cloning, recombinant expression, and the like. Thus as used herein, recombinant proteins, for example, refers to proteins produced by a recombinant host, expressing DNAs which have been added to that host through the efforts of human beings.

A "fragment" of a nucleic acid molecule or nucleotide sequence is a portion of the nucleic acid that is less than full-length and comprises at least a minimum length capable of hybridizing specifically with the nucleotide sequence of SEQ ID NO:1 or 3 under stringent hybridization conditions. The length of such a fragment is preferably 15-17 nucleotides or more.

A "variant" nucleic acid molecule or DNA molecule refers to DNA molecules containing minor changes in the native nucleotide sequence encoding the invention polypeptide(s), i.e., changes in which one or more nucleotides of a native sequence is deleted, added, and/or substituted, preferably while substantially maintaining the biological activity of the native nucleic acid molecule. Variant DNA molecules can be produced, for example, by standard DNA mutagenesis techniques or by chemically synthesizing the variant DNA molecule or a portion thereof. Generally, differences are limited so that the nucleotide sequences of the reference and the variant are closely similar overall and, in many regions, identical.

Changes in the nucleotide sequence of a variant polynucleotide may be silent. That is, they may not alter the amino acids encoded by the polynucleotide. Where alterations are limited to silent changes of this type, a variant will encode a polypeptide with the same amino acid sequence as the reference.

Alternatively, the changes may be "conservative." Conservative variants are changes in the nucleotide sequence that may alter the amino acid sequence of a polypeptide encoded by the reference polynucleotide. Such nucleotide changes may result in amino acid substitutions, additions, deletions, fusions and truncations in the polypeptide encoded by the reference sequence. Thus, conservative variants are those changes in the protein-coding region of the gene that result in conservative change in one or more amino acid residues of the polypeptide encoded by the nucleic acid sequence, i.e. amino acid substitution.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

Preferably, a variant form of the preferred nucleic acid molecule has at least 70%, more preferably at least 80%, and most preferably at least 90% nucleotide sequence similarity with the native gene encoding the invention receptor protein.

"Primer" or "nucleic acid polymerase primer(s)" refers to an oligonucleotide, whether natural or synthetic, capable of acting as a point of initiation of DNA synthesis under conditions in which synthesis of a primer extension product complementary to a nucleic acid strand is initiated, i.e., in the presence of four different nucleotide triphosphates and an agent for polymerization (i.e., DNA polymerase or reverse transcriptase) in an appropriate buffer and at a suitable temperature. The exact length of a primer will depend on many factors, but typically ranges from 15 to 25 nucleotides. Short primer molecules generally require cooler temperatures to form sufficiently stable hybrid complexes with the template. A primer need not reflect the exact sequence of the template, but must be sufficiently complementary to hybridize with a template. A primer can be labeled, if desired.

Nucleic acid amplification techniques, which are well known in the art, can be used to locate splice variants of the invention receptor protein. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns that correspond to different splice variants of transcripts encoding the invention receptor protein. Techniques for nucleic-acid manipulation are described generally in, for example, Sambrook et al. (1989) and Ausubel et al. (1987, with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103: 3185, 1981. Chemical synthesis of nucleic acids can be performed, for example, on commercial automated oligonucleotide synthesizers.

"Invention PKG" refers to the novel PKGs encoded by the herein disclosed nucleic acid molecules. Likewise, "Invention nucleic acids " or "Invention nucleic acid molecules " refer to the nucleic acid molecules of SEQ ID NO:1 and 3.

As used herein, a nucleic acid "probe" is single-stranded DNA or RNA, or analog thereof, that has a sequence of nucleotides that includes at least 14, preferably at least 20, more preferably at least 50, contiguous bases that are the same as or the complement of any 14 or more contiguous bases set forth in any of SEQ ID NO:1, or SEQ ID NO:3. In addition, the entire cDNA encoding region of the invention polypeptide, or the entire sequence corresponding to SEQ ID NO:1 or 3 may be used as a probe.

Presently preferred probe-based screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology.

Preferably, hybridization conditions will be selected which allow the identification of sequences having at least 70% homology with the probe, while discriminating against sequences which have a lower degree of homology with the probe. As a result, nucleic acids having substantially the same nucleotide sequence as the sequence of nucleotides set forth in one of SEQ ID NOs. 1 or 3. are obtained.

After screening a library, positive clones are identified by detecting a hybridization signal; the identified clones are characterized by restriction enzyme mapping and/or DNA sequence analysis, and then examined, by comparison with the sequences set forth herein, to ascertain whether they include DNA encoding the entire invention PKGs. If the selected clones are incomplete, they may be used to rescreen the same or a different library to obtain overlapping clones. If desired, the library can be rescreened with positive clones until overlapping clones that encode an entire invention peptide are obtained. If the library is a cDNA library, then the overlapping clones will include an open reading frame. If the library is genomic, then the overlapping clones may include exons and introns. In both instances, complete clones may be identified by comparison with the DNA and encoded proteins provided herein.

Thus, the nucleic acid probes are useful for various applications. On the one hand, they may be used as PCR primers for amplification of nucleic acid molecules according to the invention. On the other hand, they can be useful tools for the detection of the expression of molecules according to the invention in target tissues, for example, by in-situ hybridization or Northern-Blot hybridization.

The invention probes may be labeled by methods well-known in the art, as described hereinafter, and used in various diagnostic kits.

A "label" refers to a compound or composition that facilitates detection of a compound or composition with which it is specifically associated, which can include conferring a property that makes the labeled compound or composition able to bind specifically to another molecule. "Labeled" refers to a compound or composition that is specifically associated, typically by covalent bonding but non-covalent interactions can also be employed to label a compound or composition, with a label. Thus, a label may be detectable directly, i.e., the label can be a radioisotope (e.g., $^3$H, $^{14}$C, $^{32}$P, $^{35}$S, $^{125}$I, $^{131}$I) or a fluorescent or phosphorescent molecule (e.g., FITC, rhodamine, lanthanide phosphors), or indirectly, i.e., by enzymatic activity (e.g., horseradish peroxidase, beta-galactosidase, luciferase, alkaline phosphatase) or by its ability to bind to another molecule (e.g., streptavidin, biotin, an antigen, epitope, or antibody). Incorporation of a label can be achieved by a variety of means, i.e., by use of radiolabeled or biotinylated nucleotides in polymerase-mediated primer extension reactions, epitope-tagging via recombinant expression or synthetic means, or binding to an antibody.

Labels can be attached directly or via spacer arms of various lengths, i.e., to reduce steric hindrance. Any of a wide variety of labeled reagents can be used for purposes of the present invention. For instance, one can use one or more labeled nucleoside triphosphates, primers, linkers, or probes. A description of immunofluorescent analytic techniques is found in DeLuca, "Immunofluorescence Analysis", in Antibody As a Tool, Marchalonis et al., eds. John Wiley & Sons, Ltd., pp. 189-231 (1982), which is incorporated herein by reference.

The term label can also refer to a "tag", which can bind specifically to a labeled molecule. For instance, one can use biotin as a tag and then use avidinylated or streptavidinylated horseradish peroxidase (HRP) to bind to the tag, and then use a chromogenic substrate (e.g., tetramethylbenzamine) to detect the presence of HRP. In a similar fashion, the tag can be an epitope or antigen (e.g., digoxigenin), and an enzymatically, fluorescently, or radioactively labeled antibody can be used to bind to the tag.

The phrase "stringent hybridization" is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C.-16.6(\log_{10}[Na^+])+0.41(\% G+C)-600/1,$$

where 1 is the length of the hybrid in nucleotides. $T_m$ decreases approximately 1°-1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhart's solution, 5×SSPE, 0.2% SDS at 42° C., followed by washing in 0.2× SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5× Denhart's solution, 6×SSPE, 0.2% SDS at 42° C., followed by washing in 1×SSPE, 0.2% SDS, at 50° C.

Denhardt's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of $NaH_2PO_4$ and 7.4 g EDTA in 800 ml of water, adjusting the pH to 7.4, and then adding water to 1 liter. Denhardt's solution (see, Denhardt (1966) Biochem. Biophys. Res. Commun. 23:641) can be prepared, for example, as a 50× stock solution by mixing 5 g Ficoll (Type 400, Pharmacia LKB Biotechnology, INC., Piscataway N.J.), 5 g of polyvinylpyrrolidone, and 5 g bovine serum albumin (Fraction V; Sigma, St. Louis Mo.), and then adding water to 500 ml and filtering to remove particulate matter.

Polypeptides

The novel PKGs of the present invention are of protozoal origin; in particular the enzyme is present in, but not restricted to, protozoa of the apicomplexan family, and more specifically in *Eimeria* sp. The native *Eimeria maxima* PKG of the present invention is a protein of about 113537 kDa, and having about 1007 amino acids. The native PKG from *Plasmodium falciparum* is approximately 97693 kDa and having about 853 amino acids.

The PKG of the present invention includes a crude extract of the soluble protein, a PKG purified fraction isolated from a protozoan parasite (native enzyme), affinity purified native PKG (purified from a soluble extract using cGMP, substrate based peptides, inhibitor based molecules or antibodies) as well as a PKG produced by recombinant DNA technology (recombinant expressed enzyme).

The term "PKG purified fraction" as used herein, refers to a PKG polypeptide which is free of most other proteins, lipids, carbohydrates, nucleic acids, or other materials with which it is naturally associated. One skilled in the art can purify PKG using standard techniques for protein purification. The PKG purified fraction will yield a major band on a reducing polyacrylamide gel. The sequence of the polypeptide can be determined by amino acid sequencing.

The protozoal PKGs of the present invention include a polypeptide of SEQ ID NO:2, and a polypeptide of SEQ ID NO:4, as well as functional polypeptides and fragments thereof.

As used herein, the term "functional polypeptides and fragments" refers to a polypeptide which possesses PKG activity. Minor modifications of the PKG primary amino acid sequence may result in proteins which have substantially equivalent activity as compared to the PKG polypeptide described herein. Such modifications may be deliberate, as by site-directed mutagenesis, or may be spontaneous. All of the polypeptides produced by these modifications are included herein as long as the enzymatic activity of PKG is present. Further, deletion of one or more amino acids can also result in a modification of the structure of the resultant molecule without significantly altering its kinase activity. This can lead to the development of a smaller active molecule which may have broader utility. For example, it is possible to remove amino or carboxyl terminal amino acids which may not be required for kinase activity. Smaller peptides containing the biological activity of PKG are included in the invention.

The PKG polypeptide of the invention also includes conservative variations of the polypeptide sequence which do not substantially alter the biological activity of the protein. The term "conservative variation" as used herein denotes the replacement of an amino acid residue by another, biologically similar residue. Examples of conservative variations include the substitution of one hydrophobic residue such as isoleucine, valine or leucine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that the activity of the enzyme is not substantially altered.

Polynucleotides

The invention also provides isolated nucleic acid molecules comprising a nucleotide sequence as set forth in either one of SEQ ID NO:1 or 3. As used herein, "polynucleotide" refers to a polydeoxyribonucleotides or polyribonucleotides, in the form of a separate fragment or a larger construct, and includes DNA, cDNA and RNA sequences which encode protozoal PKG. It is understood that all polynucleotides encoding all or a portion of the herein disclosed protozoal PKGs are also included herein, as long as they encode a polypeptide with PKG kinase activity. Such polynucleotides include naturally occurring, synthetic, and intentionally manipulated polynucleotides. For example, PKG polynucleotide may be subjected to site-directed mutagenesis.

It is known that there is a substantial amount of redundancy in the various codons which code for specific amino acids. There are 20 natural amino acids, most of which are specified by more than one codon. Therefore, this invention is also directed to those DNA sequences which contain alternative codons which code for the eventual translation of the identical amino acid. For purposes of this specification, a sequence bearing one or more replaced codons will be defined as a degenerate variation. Therefore, the present invention discloses codon redundancy which may result in differing DNA molecules expressing an identical protein.

Splice variants of the isolated DNA molecules are also an object of the invention. Typically, unless the invention PKGs arise as a splice variant, each PKG-encoding DNA will share substantial sequence homology (i.e., greater than about 90%), with the PKG-encoding DNA described herein. DNA or RNA encoding a splice variant may share less than 90% overall sequence homology with the DNA or RNA provided herein, but such a splice variant would include regions of nearly 100% homology to the disclosed DNAs.

Specifically disclosed herein is a cDNA sequence comprising the nucleotide sequence of SEQ. ID NO:1 containing the predicted coding region for *Eimeria maxima* PKG. The cDNA encodes a protein of about 1007 amino acids.

Also disclosed herein is a cDNA sequence comprising the nucleotide sequence as set forth in SEQ. ID NO:3 containing the predicted coding region for *Plasmodium falciparum* PKG. The cDNA includes an open reading frame encoding a protein of about 853 amino acids.

The polynucleotides (nucleic acid molecules) encoding the invention PKG molecules, i.e., the *Eimeria maxima* and *Plasmodium falciparum* PKG include the nucleotide sequences SEQ ID NO:1 and SEQ ID NO:3, as well as nucleic acid sequences complementary to that sequence. A complementary sequence may include an antisense nucleotide. When the sequence is RNA, the deoxynucleotides A, G, C, and T are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the proteins of the present invention including PKG of SEQ ID NO:2 and SEQ ID NO:4.

Any of a variety of procedures may be used to clone the invention PKGs. These methods include, but are not limited to, (1) RACE PCR cloning technique (Frohman, et al., 1988, *Proc. Natl. Acad. Sci.* 85: 8998-9002). 5' and/or 3' RACE may be performed to generate a full length cDNA sequence. This strategy involves using gene-specific oligonucleotide primers for PCR amplification of PKG cDNA. These gene-specific primers are designed through identification of an expressed sequence tag (EST) nucleotide sequence which has been identified by searching any number of publicly available nucleic acid and protein databases;

(2) direct functional expression of the PKG cDNA following the construction of a PKG-containing cDNA library in an appropriate expression vector system;

(3) screening a PKG-containing cDNA library constructed in a bacteriophage or plasmid vector with a labeled degenerate oligonucleotide probe designed from the amino acid sequence of the PKG protein;

(4) screening a PKG-containing cDNA library constructed in a bacteriophage or plasmid vector with a partial cDNA encoding the PKG protein. This partial cDNA is obtained by the specific PCR amplification of PKG DNA fragments through the design of degenerate oligonucleotide primers from the amino acid sequence known for other kinases which are related to the PKG protein;

(5) screening a PKG-containing cDNA library constructed in a bacteriophage or plasmid vector with a partial cDNA encoding the PKG protein. This strategy may also involve using gene-specific oligonucleotide primers for PCR amplification of PKG cDNA identified as an EST as described above; or (6) designing 5' and/or 3' gene specific oligonucleotides using SEQ ID NO:1 or SEQ ID NO:3 as a template so that either the full length cDNA may be generated by known PCR techniques, or a portion of the coding region may be generated by these same known PCR techniques to generate and isolate a portion of the coding region to use as a probe to screen one of numerous types of cDNA and/or genomic libraries in order to isolate a full length version of the nucleotide sequence encoding PKG.

It is readily apparent to those skilled in the art that suitable cDNA libraries may be prepared from cells or cell lines which have PKG activity. The selection of cells or cell lines for use in preparing a cDNA library to isolate a PKG cDNA may be done by first measuring cell associated PKG activity using any known assay for PKG activity.

Preparation of cDNA libraries can be performed by standard techniques well known in the art. Well known cDNA library construction techniques can be found for example, in Sambrook, et al., 1989, *Molecular Cloning: A Laboratory Manual;* Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding the invention PKGs may also be isolated from a suitable genomic DNA library. Construction of genomic DNA libraries can be performed by standard techniques well known in the art. Well known genomic DNA library construction techniques can be found in Sambrook, et al., supra. Genomic DNA libraries may also be obtained from numerous commercial sources, including but not limited to Clontech Laboratories, Inc. and Stratagene.

In order to clone the PKG gene by one of the preferred methods, the amino acid sequence or DNA sequence of PKG or a homologous protein may be necessary. To accomplish this, the PKG or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial PKG DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the PKG sequence but others in the set will be capable of hybridizing to PKG DNA even in the presence of DNA oligonucleotides with mismatches. The mismatched DNA oligonucleotides may still sufficiently hybridize to the PKG DNA to permit identification and isolation of PKG encoding DNA.

Alternatively, the nucleotide sequence of a region of an expressed sequence may be identified by searching one or more available databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO:1 or SEQ ID NO:3, either for the purpose of isolating overlapping 5' and 3' RACE products for generation of a full-length sequence coding for PKG, or to isolate a portion of the nucleotide sequence coding for PKG for use as a probe to screen one or more cDNA- or genomic-based libraries to isolate a full-length sequence encoding PKG or PKG-like proteins.

DNA sequences of the invention can be obtained by several methods. For example, the DNA can be isolated using hybridization techniques which are well known in the art. These include, but are not limited to: 1) hybridization to genomic or cDNA libraries with probes to detect homologous nucleotide sequences; 2) antibody screening of expression libraries to detect cloned DNA fragments with shared structural features; and 3) PCR amplification of a desired nucleotide sequence using oligonucleotide primers. Preferably the PKG polynucleotide of the invention is derived from a protozoal organism, and most preferably from an *Eimeria* species. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known.

The DNA sequence encoding the protein can be deduced from the genetic code; however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

The development of specific DNA sequences encoding PKG can also be obtained by: 1) isolation of double-stranded DNA sequences from genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form.

A preferred method for obtaining genomic DNA for example is the Polymerase Chain Reaction (PCR), which relies on an in vitro method of nucleic acid synthesis by which a particular segment of DNA is specifically replicated. Two oligonucleotide primers that flank the DNA fragment to be amplified are utilized in repeated cycles of heat denaturation of the DNA, annealing of the primers to their complementary sequences, and extension of the annealed primers with DNA polymerase. These primers hybridize to opposite strands of the target sequence and are oriented so that DNA synthesis by the polymerase proceeds across the region between the primers. Since the extension products themselves are also complementary to and capable of binding primers, successive cycles of amplification essentially double the amount of the target DNA synthesized in the previous cycle. The result is an exponential accumulation of the specific target fragment, approximately 2<n>, where n is the number of cycles of amplification performed (see PCR Protocols, Eds. Innis, et al., Academic Press, Inc., 1990, incorporated herein by reference).

A cDNA expression library, in a vector such as lambda gt11, can be screened indirectly for PKG peptides having at least one epitope, using antibodies specific for PKG. Such antibodies can be either polyclonally or monoclonally derived and used to detect an expression product indicative of the presence of a PKG cDNA. The polynucleotide sequence for PKG also includes sequences complementary to the polynucleotide encoding PKG (antisense sequences). Antisense nucleic acids are DNA or RNA molecules that are complementary to at least a portion of a specific mRNA molecule (Weintraub, Scientific American, 262:40, 1990). The invention embraces all antisense polynucleotides capable of inhibiting the production of the PKG polypeptides of the invention.

In the cell, the antisense nucleic acids hybridize to the corresponding mRNA, forming a double-stranded molecule. The antisense nucleic acids may interfere with the translation of the mRNA since the cell will not translate a mRNA that is double-stranded, or alternatively, the double-stranded mRNA is targeted for degradation. Antisense oligomers of about 15 nucleotides are preferred, since they are easily synthesized, small enough to enter the cell, and are less likely to cause problems than larger molecules when introduced into the target PKG-producing cell. The use of antisense methods to inhibit the translation of genes is well known in the art (Marcus-Sakura, Anal. Biochem., 172:289, 1988).

Vectors, Host Cells, Expression

DNA sequences encoding the invention PKGs can be expressed in vitro by DNA transfer into a suitable host cell. "Host cells" are cells in which a vector carrying DNA sequences of interest can be propagated and the protein coded for by the DNA sequences can be expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

A variety of expression vectors may be used to express recombinant invention PKGs in host cells. "Expression vectors" are DNA sequences that are required for the transcription of cloned DNA and the translation of their mRNAs in an appropriate host. Such vectors can be used to express eukaryotic DNA in a variety of hosts such as bacteria, blue green algae, plant cells, insect cells, apicomplexan parasites and animal cells. Specifically designed vectors allow the shuttling of DNA between hosts such as bacteria-yeast, bacteria-insect cells, bacteria-apicomplexan parasites or bacteria-animal cells. An appropriately constructed expression vector should contain: an origin of replication for autonomous replication in host cells, selectable markers, a limited number of useful restriction enzyme sites, a potential for high copy number, and active promoters. Other expression vectors do not contain an origin of replication for autonomous replication in host cells but rather depend on the ability of the vector to stably integrate (either randomly or by a homologous integration event) using a marker to select for integration/maintenance. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

Commercially available mammalian expression vectors which may be suitable for recombinant PKG expression, include but are not limited to, pcDNA3, pcDNA3.1, pcDNAI, pcDNAIamp (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant invention PKGs in bacterial cells. Commercially available bacterial expression vectors which may be suitable for recombinant PKG expression include, but are not limited to pCR2.1 (Invitrogen), pET11a (Novagen), lambda gt11 (Invitrogen), pcDNAII (Invitrogen), pKK223-3 (Pharmacia), and pQE vectors (Qiagen).

A variety of fungal cell expression vectors may be used to express recombinant invention PKGs in fungal cells. Commercially available fungal cell expression vectors which may be suitable for recombinant PKG expression include but are not limited to pYES2 (Invitrogen), *Pichia* expression vector (Invitrogen).

A variety of insect cell expression vectors may be used to express recombinant invention PKGs in insect cells. Commercially available insect cell expression vectors which may be suitable for recombinant expression of PKG include but are not limited to pBlueBacIII, pBlueBacHis2 (Invitrogen) and pFastBac1, pFastBacHT (Life Technologies).

A variety of expression vectors may be used to express recombinant invention PKGs in apicomplexan parasites, most notably *Toxoplasma gondii*. Expression vectors which may be suitable for recombinant expression of PKG include but are not limited to pminCAT/HXGPRT-, pDBFR-TSc3/M3, pDHFR-TSc3/M2M3, pminiHXGPRT, and pminP30/G (NIH AIDS Research and Reference Reagent Program).

The expression vector may be introduced into host cells via any one of a number of techniques including but not limited to infection, transformation, transfection, lipofection, protoplast fusion, and electroporation. The expression vector-containing cells are clonally propagated and individually analyzed to determine whether they produce PKG protein. Identification of PKG expressing host cell clones may be done by several means, including but not limited to immunological reactivity with anti-PKG antibodies.

Expression of a PKG encoding DNA may also be performed using in vitro produced synthetic mRNA or native mRNA. Synthetic mRNA or mRNA isolated from PKG producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

A variety of host-expression vector systems may be utilized to express the PKG coding sequence. These include but are not limited to microorganisms such as bacteria transformed with recombinant bacteriophage DNA, plasmid DNA or cosmid DNA expression vectors containing a PKG encoding coding sequence; yeast transformed with recombinant yeast expression vectors containing the PKG coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the PKG coding sequence; insect cell systems infected with recombinant virus expression vectors (e.g., baculovirus) containing the PKG coding sequence; or animal cell systems infected with recombinant virus expression vectors (e.g., retroviruses, adenovirus, vaccinia virus) containing the PKG coding sequence, or transformed animal cell systems engineered for stable expression.

To determine the PKG cDNA sequence(s) that yields optimal levels of an invention PKG protein, PKG cDNA molecules including but not limited to the following can be constructed: the full-length open reading frame of the respective PKG cDNA and various constructs containing portions of the cDNA encoding only specific domains of the protein or rearranged domains of the protein. All constructs can be designed to contain none, all or portions of the 5' and/or 3' untranslated region of PKG. PKG activity and levels of protein expression can be determined following the introduction, both singly and in combination, of these constructs into appropriate host cells. Following determination of the PKG cDNA cassette yielding optimal expression in transient assays, this PKG cDNA construct is transferred to a variety of expression vectors (including recombinant viruses), including but not limited to those for mammalian cells, plant cells, insect cells, oocytes, bacteria, and yeast cells.

The protein coding region of the recombinant PKG coding sequence(s) of the invention may also be modified at the level of the cDNA to add epitope tags. Modification of the cDNA sequence is usually but not exclusively directed to the amino- or carboxy-terminal end of the protein coding region. This is accomplished by any of several methods common in the art. Examples of modifications include but are not limited to the influenza viral HA tag, the FLAG tag, a hexahistidine tag, the c-myc tag, as well as fusions with maltose binding protein, glutathione transferase and green fluorescent protein. These tags can serve as a means to distinguish recombinant PKG from host PKG immunologically using commercially available antisera to the tag sequences and as a purification tool to resolve recombinant from host PKG.

The levels of recombinant PKG protein in host cells is quantified by a variety of techniques including, but not limited to, immunoaffinity and/or ligand affinity techniques. PKG-specific antibody affinity beads or PKG-specific antibodies are used to isolate PKG protein metabolically labeled with radioactive amino acids such as [3H]-leucine or [35S]-methionine or unlabelled PKG protein. Labeled PKG protein is analyzed by SDS-PAGE. Unlabelled PKG protein is detected by Western blotting, ELISA or RIA assays employing PKG-specific or epitope tag-specific antibodies.

Purification of PKG

Following expression of PKG in a host cell, i.e., any one or both of the herein described invention PKGs, the resulting PKG protein may be recovered to provide PKG in active form. Several PKG purification procedures are available and suitable for use. Recombinant PKG may be purified from cell lysates and extracts, or from conditioned culture medium, by various combinations of, or individual application of salt fractionation, ion exchange chromatography, size exclusion chromatography, hydroxyapatite adsorption chromatography, hydrophobic interaction chromatography and cyclic nucleotide affinity chromatography.

In addition, recombinant PKG can be separated from other cellular proteins by use of an immuno-affinity column made with monoclonal or polyclonal antibodies specific for full length PKG, or polypeptide fragments of PKG. Additionally, polyclonal or monoclonal antibodies may be raised against a synthetic peptide (usually from about 9 to about 25 amino acids in length) from a portion of the protein.

Monospecific antibodies to an invention PKG are purified from mammalian antisera containing antibodies reactive against PKG or are prepared as monoclonal antibodies reactive with PKG using the technique of Kohler and Milstein (1975, *Nature* 256: 495-497). Monospecific antibody as used herein is defined as a single antibody species or multiple antibody species with homogenous binding characteristics for PKG. Homogenous binding as used herein refers to the ability of the antibody species to bind to a specific antigen or epitope, such as those associated with the PKG, as described above. PKG specific antibodies are raised by immunizing animals such as mice, rats, guinea pigs, rabbits, goats, horses and the like, with an appropriate concentration of PKG or PKG synthetic peptide either with or without an immune adjuvant.

Preimmune serum is collected prior to the first immunization. Each animal receives between about 0.1 µg and about 1000 µg of PKG associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the PKG protein or PKG synthetic peptide in, preferably, Freund's complete adjuvant at multiple sites either subcutaneously (SC), intraperitoneally (1P) or both. Each animal is bled at regular intervals, preferably weekly, to determine antibody titer. The animals may or may not receive booster injections following the initial immunization. Those animals receiving booster injections are generally given an equal or smaller amount of PKG in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with PKG are prepared by immunizing inbred mice, preferably Balb/c, with an invention PKG. The mice are immunized by the IP or SC route with about 1 µg to about 100 µg, preferably about 10 µg, of PKG in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 µg of the same PKG antigen in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using PKG as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8-12 days after cell transfer and the monoclonal antibodies are purified by techniques known in the art.

In vitro production of anti-PKG monoclonal antibody is carried out by growing the hydridoma in DMEM containing about 2% fetal calf serum to obtain sufficient quantities of the specific monoclonal antibody. The monoclonal antibodies are purified by techniques known in the art.

Antibody titers of ascites or hybridoma culture fluids are determined by various serological or immunological assays which include, but are not limited to, precipitation, passive agglutination, enzyme-linked immunosorbent antibody ELISA) technique and radioimmunoassay (RIA) techniques. Similar assays are used to detect the presence of PKG in body fluids or tissue and cell extracts.

It is readily apparent to those skilled in the art that the above described methods for producing monospecific antibodies may be utilized to produce antibodies specific for PKG polypeptide fragments, or full-length PKG polypeptide.

PKG antibody affinity columns are made by adding the antibodies to AFFIGEL 10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1 M ethanolamine HC1 (pH 8). The column is washed with water followed by 0.23 M glycine HC1 (pH 2.6) to remove any non-conjugated antibody or extraneous protein. The column is then equilibrated in phosphate buffered saline (pH 7.3) and the cell culture supernatants or cell extracts containing PKG or PKG fragments are slowly passed through the column. The column is then washed with phosphate buffered saline until the optical density ($A_{280}$) falls to background, then the protein is eluted with 0.23 M glycine-HCl (pH 2.6). The purified PKG protein is then dialyzed against phosphate buffered saline.

One skilled in the art will appreciate that many of the above described procedures for purification of recombinant expressed PKG are also suitable for purification of the native enzyme from a protozoan parasite.

Inhibitors—Assays and Molecules

In another aspect of the present invention there is provided a method for identifying compounds having antiprotozoal activity. In one embodiment said method comprises:
 (a) contacting protozoal PKG of the invention with (i) a known amount of a labeled compound that interacts with a PKG and (ii) a known dilution of a test compound or a natural product extract; and
 (b) quantitating the percent inhibition of interaction of said labeled compound induced by said test compound.

The PKG may be a purified or partially purified native enzyme, a cloned PKG or an engineered variant thereof, a crude preparation of the enzyme, or an extract containing PKG activity. Fragments of PKG that retain the desired enzyme activity are also within the scope of the invention.

A compound that interacts with an invention PKG may be one that is a substrate for the enzyme, or one that binds to the enzyme either at its active site or at an alternate site (e.g., the cGMP binding domains) that results in altered enzyme activity. A substrate may be a generic protein kinase substrate (e.g., myosin basic protein, MBP), a synthetic peptide or other naturally occurring substrates. Examples of compounds that bind to PKG are known inhibitors such as KT5823, synthetic or naturally occurring peptides as well as other small molecule (i.e. non-peptidyl) inhibitors such as 2-(4-fluorophenyl)-5-(N-methylpiperidin-4-yl)-3-(4-pyridyl)pyrrole, which will be referred to herein as "Inhibitor Compound". The Inhibitor Compound and its preparation are disclosed in U.S. Pat. No. 5,792,778. The compound that interacts with PKG is preferably labeled to allow easy quantitation of the level of interaction between the compound and the enzyme. Preferred radiolabels are [$^{14}$C] or [$^{3}$H]. The tritiated Inhibitor Compound may be prepared as follows:

A solution of Inhibitor Compound (as the free amine, 2.5 mg, 0.007 mmol) in DMSO (0.8 ml) was stirred for half-hour at room temperature. High specific activity tritium labeled methyl iodide (200 mCi, 0.0026 mmol, at 80 Ci/mmol in 0.4 ml toluene solution) was added to this mixture and the resulting clear solution was stirred for 24 hour. The product was diluted with isopropanol (35 mL) evaporated to near dryness and dissolved with 3 mL of methanol for HPLC purification. The product was collected into a vial containing 7 mL of cold water (chilled in the refrigerator before use). After assay for radioactivity and radio-purity, the sample was stored in the refrigerator to prevent decomposition. Total activity of the purified product was 45 mCi and at specific activity of 68 Ci/mmol (by UV spectrum measurement). HPLC conditions are: ZORBAX SB-C18 Semi-prep column (5 um, 9.4 mmI.D..times.250 mm), 65/35/0.1 (v/v/v) water/acetonitrile/HClO4. UV-detection at 230 nm, 4.5 mL/min, Rt=24.5 min, radiochemical purity: 98.5%

The test compound may be a synthetic compound, a purified preparation, crude preparation, or an initial extract of a natural product obtained from plant, microorganism or animal sources.

One particular embodiment of the present method is based on test compound induced inhibition of PKG activity. The enzyme inhibition assay involves adding PKG or an extract containing PKG to mixtures of enzyme substrates (one of which is radiolableled) and the test compound, each of which are present in known concentrations. The amount of the enzyme is chosen such that less than 20% of the radiolabeled substrate (usually [$^{32}$P] or [$^{33}$P]-ATP,) is consumed during the assay. The assay is carried out with the test compound at a series of different dilution levels. After a period of incubation, the labeled portion of the ATP substrate becomes covalently attached by enzymatic action to the peptide or protein substrate. This reaction product is separated from unincorporated precursor and counted. The assay is generally carried out in parallel with a control (no test compound) and a positive control (containing a known enzyme inhibitor instead of a test compound). The concentration of the test compound at which 50% of the enzyme activity is inhibited (IC$_{50}$) is determined using a recognized method.

Although enzyme inhibition is the most direct measure of the inhibitory activity of the test compound, the present inventors have found that results obtained from competitive binding assay in which the test compound competes with a known inhibitor for binding to the enzyme active site correlate well with the results obtained from enzyme inhibition assay described above.

Accordingly, another particular embodiment of the present method is based on competitive binding of test compound and a known PKG inhibitor. The binding assay represents a more convenient way to assess enzyme inhibition since it allows the use of a crude extract containing PKG rather than partially purified enzyme. The use of a crude extract may not always be suitable in the enzyme inhibition assay because other enzymes present in the extract may phosphorylate the test substrate. The competition binding assay is carried out by adding the PKG or an extract containing PKG activity to a mixture of the test compound and a labeled inhibitor, both of which are present in the mixture in known concentrations. After incubation, the enzyme-inhibitor complex is separated from the unbound labeled inhibitors and unlabeled test compound, and counted. The concentration of the test compound required to inhibit 50% of the binding of the labeled inhibitor to the PKG (IC$_{50}$) is calculated.

In a preferred embodiment, the method of the present invention utilizes a recombinant PKG, a native PKG, or an extract containing PKG obtained from a protozoal source, such as *Eimeria, Toxoplasma* or *Plasmodium* sp.

In a more preferred embodiment, the method of the present invention further comprises determining the IC50 of test compounds against host PKG in either the enzyme inhibition assay or the binding assay as described above, to identify those compounds that have selectivity for parasitic PKG over that of a host. The assays are the same as previously described, with the PKG activity obtained from a host of protozoa; for example the host PKG may be obtained from a mammalian source, e.g. human, or an avian source, e.g. chicken.

Another method useful to identify inhibitors that are selective for parasitic PKG is the use of an in gel kinase assay to determine the level of substrate phosphorylation catalyzed by parasite PKG relative to host PKG or other cellular kinase activities. Thus compounds that specifically inhibit phosphorylation of a test substrate (e.g., myelin basic protein) by parasite PKG and not a host PKG, would be considered selective parasitic PKG inhibitors.

Where the enzyme inhibition or binding assay utilizes a crude preparation or an extract containing PKG, the target of the test compound may be verified by examining the level of native substrate phosphorylation. Thus, the intact host or parasitic cell containing the enzyme is treated with the test compound. Alternatively, intact host or parasite cells containing the enzyme are treated with test compound in the presence of labeled phosphate ([$^{33}$P] or [$^{32}$P] is the preferred label). In both cases the cells are lysed, soluble proteins are partially purified, and analyzed by two dimensional polyacrylamide electrophoresis. Proteins are detected by staining or by detection of radiolabel by autoradiography or fluorography. Differentially phosphorylated species can readily be distinguished on such gels due to the altered migration of multiply phosphorylated proteins or by the presence/absence of an autoradiographic signal. A PKG inhibitor will block the incorporation of radiolabeled phosphate into substrate. Since this technique uses intact cells treated with the test compound, this technique may also be used to identify prodrugs that may be converted to a PKG inhibitor within the cellular environment, but may not be so identified by assay based on the enzyme itself.

Another embodiment of the method for identifying compounds having antiprotozoal activity comprises:

(a) contacting an intact host or protozoal cell with a test compound or a natural product extract;

(b) disrupting said cell to obtain a biochemical fraction possessing PKG catalytic activity; and (c) determining the level of PKG activity in said biochemical fraction.

Thus intact host cell(s) are treated with a test compound at a known concentration (or a natural product extract at know dilution) for 1 minute to 12 hours. Thereafter the host cells are lysed, for example, using the method described in Example 3 or other known methods in the art. The level of PKG catalytic activity may be determined using methods hereinafter described in the Examples as well as other methods generally known by those skilled in the art.

Compounds identified as PKG inhibitors may be useful as antiprotozoal agents, and as such, they may be used in the treatment and prevention of protozoal diseases in human and animals, including poultry. Thus, PKG inhibitors may be administered to a host suffering from a protozoal infection a therapeutically effective amount of a compound which inhibits PKG. A therapeutically effective amount may be one that is sufficient to inhibit PKG of the causative protozoa.

PKG inhibitors are preferably used in the treatment or prevention of protozoal infections caused by a member of the sub-phyllum Apicomplexa. PKG inhibitors are also preferably used in the treatment or prevention of malaria, toxoplasmosis, cryptosporidiosis and trypanosomiasis in humans and animals; and in the management of coccidiosis, particularly in poultry, either to treat coccidial infection or to prevent the occurrence of such infection.

In the case that a PKG inhibitor is expected to be administered on a chronic basis, such as in the prevention of coccidiosis in poultry, the PKG inhibitor preferably is selective for protozoal over the host PKG activity. Long term administration of such a selective inhibitor would minimize adverse effects to the host due to PKG inhibition.

Two specific examples of using PKG inhibitors to prevent the establishment of parasitic infections in humans and animals are 1) the prevention of *Plasmodium* (malaria) infection in humans in endemic areas and 2) the prevention of coccidiosis in poultry by administering the compound continuously in the feed or drinking water.

Malaria is the number one cause of death in the world. The disease is transmitted by mosquitoes in endemic areas and can very rapidly progress to a life threatening infection. Therefore, individuals living in or visiting areas where malaria carrying mosquitoes are present routinely take prophylactic drugs to prevent infection. The PKG inhibitor would be administered orally or parenterally one or more time(s) a day. The dose would range from 0.01 mg/kg to 100 mg/kg. The compound could be administered for the entire period during which the patient or animal is at risk of acquiring a parasitic infection.

Coccidiosis is a disease which can occur in humans and animals and is caused by several genera of coccidia. The most economically important occurrence of coccidiosis is the disease in poultry. Coccidiosis in poultry is caused by protozoal parasites of the genus *Eimeria*. The disease can spread quite rapidly throughout flocks of birds via contaminated feces. The parasites destroy gut tissue and therefore damage the gut lining impairing nutrient absorption. An outbreak of coccidiosis in a poultry house can cause such dramatic economic losses for poultry producers that it has become standard practice to use anticoccidial agents prophylactically in the feed. A PKG inhibitor would be administered in the feed or drinking water for a portion of, or the entire life of the birds. The dose would range between 0.1 ppm to 500 ppm in the feed or water.

For treatment of established parasitic infections in humans or animals, the PKG inhibitor could be administered orally or parenterally once the infection is suspected or diagnosed. The treatment period would vary according to the specific parasitic disease and the severity of the infection. In general the treatment would be continued until the parasites were eradicated and/or the symptoms of the disease were resolved.

*P. falciparum* causes acute life threatening malarial infections in humans. The infection if left untreated can quite often result in death of the patient. A malaria infection can be easily diagnosed by symptoms and examination of a blood sample from the patient. For patients in endemic areas, treatment would be initiated following diagnosis. A PKG inhibitor would be administered one or more time(s) a day, orally or parenterally, until the infection was eliminated. The dose would range between 0.01 mg/kg to 200 mg/kg.

PKG inhibitors may be administered to a host in need of treatment in a manner similar to that used for other antiprotozoal agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of protozoal diseases in human and animals, the dosage may range from 0.01 mg/kg to 500 mg/kg. For prophylactic use in human and animals, the dosage may range from 0.01 mg/kg to 100 mg/kg. For use as an anticoccidial agent, particularly in poultry, the compound is preferably administered in the animals' feed or drinking water. The dosage ranges from 0.1 ppm to 500 ppm.

PKG inhibitors may be formulated according to conventional pharmaceutical compounding techniques. Thus a PKG inhibitor composition may contain, in addition to the active ingredient, a pharmaceutically acceptable carrier and optionally other therapeutic ingredients. The composition may be one that is suitable for oral, rectal, topical, or parenteral (including subcutaneous, intramuscular, and intravenous) administrations, although the most suitable route in any given case will depend on the particular host, and nature and severity of the conditions for which the active ingredient is being administered. The composition may be conveniently presented in unit dosage form and prepared by any of the methods well-known in the art of pharmacy.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5-10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

For use in the management of coccidiosis in poultry, a PKG inhibitor may be conveniently administered as a component of a feed composition. Suitable poultry feed composition will typically contain from about 1 ppm to about 1000 ppm, preferably from about 0.01% to about 0.1% percent, by weight of a PKG inhibitor. The optimum levels will naturally vary with the species of *Eimeria* involved, and can be readily determined by one skilled in the art. Compound levels in poultry feed ranging from about 0.01% to about 0.1% percent by weight of the diet are especially useful in controlling the pathology associated with *Eimeria maxima*. Amounts of about 0.01% to about 0.1% percent by weight are advantageous in reducing the pathogenic effects of both cecal and intestinal coccidiosis.

In the preparation of poultry feed, a PKG inhibitor may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal, calcium carbonate and vitamins.

Compositions containing a compound may also be prepared in powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the combination and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound combination and may optionally include a veterinary acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The following examples are provided to illustrate the invention are not to be construed as limiting the scope of the invention in any manner.

EXAMPLE 1

(i) Cloning of cDNAs that Code for *E. maxima* and *P. falciparum* PKG

A common strategy was employed to isolate PKG cDNA clones from both *E. maxima* and *P. falciparum* parasites. The first step in the cloning strategy involved a coupled reverse transcriptase-polymerase chain reaction (RT-PCR). Using an alignment of the deduced amino acid sequence from cDNA clones coding for *E. tenella* and *T. gondii* PKG proteins, areas of sequence identity within the presumptive cGMP-binding and catalytic domains were identified. Degenerate oligonucleotide primers were synthesized based on the following four peptide sequences.

| Primer | Amino Acid Sequence | Primer Orientation | PKG Domain |
|---|---|---|---|
| a | VKFFEML (Et) SEQ ID NO.: 5 VKFFEML (Tg) SEQ ID NO.: 5 | sense | cGMP-binding |
| b | GEYFGERAL (Et) SEQ ID NO.: 6 GDYFGERAL (Tg) SEQ ID NO.: 7 | sense | cGMP-binding |
| c | RDLKPENI (Et) SEQ ID NO.: 8 RDLKPENI (Tg) SEQ ID NO.: 8 | antisense | catalytic |
| d | HYMAPEV (Et) SEQ ID NO.: 9 HYMAPEV (Tg) SEQ ID NO.: 9 | antisense | catalytic |

Total RNA purified from *E. maxima* sporulated oocysts and a trophozoite-enriched preparation of *P. falciparum* was first converted into cDNA using reverse transcriptase. The resulting cDNA products were then used as template in PCR reactions using the degenerate oligonucleotide primers from regions 'a' and 'd' above. PCR reaction products were then used as templates in secondary nested PCR reactions using degenerate primers from regions 'b' and/or 'c' above.

PCR reaction products produced in the secondary nested reactions were subcloned and subjected to DNA sequence analysis. Nucleotide sequence of the PCR products demonstrated homology to *E. tenella* and *T. gondii* PKG. The PCR products from *P. falciparum* and *E. maxima*, both of which were anchored at the nested peptide regions 'b' and 'c', are distinct from one another but do share DNA sequence homology. Due to the location of the peptides within the full length deduced protein coding sequence of *E. tenella* and *T. gondii*, these RT-PCR generated cDNA clones represent partial clones. Accordingly, the respective RT-PCR generated clones were used as hybridization probes to screen *P. falciparum* and *E. maxima* cDNA libraries to isolate full length cDNAs. The nucleotide sequence of the full length cDNA clones from both of these parasites (SEQ ID NO:1 for *E. maxima* and SEQ ID NO:3 for *P. falciparum*) and their respective deduced amino acid sequences (SEQ ID NO:2 for *E. maxima* and SEQ ID NO:4 for *P. falciparum*) are attached.

(ii) Recombinant Expression of *E. maxima* PKG in *T. gondii*

*T. gondii* was selected as a host cell for recombinant expression of functional *E. maxima* PKG enzyme. An *Eimeria maxima* cDNA encoding the PKG open reading frame (ORF) was modified prior to subcloning for expression by appending either an N-terminal or C-terminal FLAG epitope for detection purposes via PCR amplification. DNA fragments encoding FLAG-epitope tagged PKGs were then placed in a *T. gondii* expression vector under the control of a *Toxoplasma* α-tubulin promoter (Soldati and Boothroyd, 1993, *Science* 260, 349-352). The vector encodes bacterial chloramphenicol acetyltransferase (CAT) as a selectable marker for transfection.

*T. gondii* tachyzoites of the RH strain were maintained by serial passage in primary human foreskin fibroblast cultures (HFF). Host cells were grown in Dulbecco's modified Eagle's medium with 10% heat-inactivated newborn bovine serum. This culture medium was replaced with modified Eagle's medium containing 2% dialyzed fetal bovine serum immediately prior to parasite infection (Roos et al, 1994, *Methods Cell Biol.* 45, 27-63). General procedures for the transient and stable transformation of *T. gondii* by electroporation have been described (Soldati and Boothroyd, 1993, *Science* 260, 349-352, Roos et al, 1994, *Methods Cell Biol.* 45, 27-63, Kim et al, 1993, *Science* 262, 911-914). Following electroporation, stable transgenic *Toxoplasma* lines were selected with chloramphenicol (Kim et al, 1993, *Science* 262, 911-914, Black et al, 1995, *Molec. Biochem. Parasitol.* 74, 55-63) and clones expressing recombinant PKG were identified by immunofluorescence analysis with FLAG M2 antisera (Sigma). Clonal isolation was achieved by limiting dilution in 96-well plates.

Recombinant FLAG-tagged E. maxima PKG was purified from *T. gondii* lysates by FLAG immuno-affinity chromatography. Parasites from ten T- 175 culture flasks were filtered through 3 μM nucleopore membranes (Millipore) to remove host cell debris, centrifuged in 50% Percoll and washed in phosphate buffered saline (PBS). The resulting pellet was suspended in HBS lysis buffer (50 mM HEPES pH 7.4, 150 mM NaCl, 1 mM EDTA, 1% Nonidet P40, 10 mM NaF, 0.1 mM Na orthovanadate, 1 mM DTT) supplemented with a cocktail of protease inhibitors (Sigma). Following sonication with a Branson SONIFIER microtip (three 15 sec blasts with intermittent cooling), the extract was centrifuged successively at 4° C. for 10 minutes at 3000×g, and for 30 minutes at 100,000×g to remove insoluble debris. Glycerol was added to a final concentration of 10% (v/v). FLAG-epitope tagged PKG was purified using an ANTI-FLAG M2-agarose affinity gel matrix (Sigma). Matrix-immobilized recombinant enzyme was washed with lysis buffer, eluted with 0.5 mg/ml FLAG peptide, and concentrated in an ULTRAFREE Biomax-30K filter device (Millipore). Protein was measured with a micro BCA reagent (Pierce), using a TCA/sodium deoxycholate step (Brown et al, 1989, *Analytical Biochemistry* 180, 136-139) to remove residual FLAG peptide prior to quantitation. Approximately 20-30 ug of purified recombinant $_{FLAG}$PKG was obtained from ten T175 flasks of transgenic parasites.

(iii) Isolation and Characterization of Native PKG from *E. maxima*

*E. maxima* unsporulated oocysts were harvested from the ceca of chickens seven days after infection with sporulated oocysts and purified using standard methods (Schmatz et al, 1986, *J. Protozoology* 33, 109-114). Soluble extracts were prepared by vortexing $2 \times 10^9$ *E. maxima* unsporulated oocysts with an equal volume of buffer (10 mM HEPES pH 7.4, 1 mM sodium orthovanadate, 20% glycerol, 0.1 mg/ml Bacitracin and 0.5% Sigma protease inhibitor cocktail P8340), and an equal volume of 4 mM glass beads for 20 minutes. The resulting homogenate was centrifuged (100,000×g, 1 hour) and the supernatant (S100) collected. Native *E. maxima* PKG activity in the S100 fraction was affinity purified using an 8-AET-cGMP-agarose matrix as described below.

(iv) Isolation and Characterization of Native PKG from *P. falciparum*

The NF54 strain of *P. falciparum* was grown in 5% human O+ red blood cells in RPMI 1640 media supplemented with 10% heat-inactivated human serum and 3% hypoxanthine using modifications of standard conditions (Trager and Jensen, 1976, *Science* 193, 673-675). Media was changed daily and parasites were diluted into fresh erythrocytes to a parasitemia of 0.2-0.5% every 3 to 4 days; final parasitemia ranged from 4 to 10%. Synchronized cultures (Lambros and Vanderberg, 1979, *J. Parasitology* 65, 418-420) enriched for schizont and trophozoite stages were prepared in a continuous Percoll gradient (Rivadeneira et al, 1983 *J. Protozoology* 30, 367-370). Frozen enriched packed cell preparations of parasite were suspended in cold lysis buffer (50 mM Hepes pH 7.4, 150 mM NaCl, 1 mM EDTA, 1% Nonidet P-40, 10 mM NaF, 0.1 mM Na orthovanadate, 1 mM DTT) supplemented with a cocktail of protease inhibitors (Sigma).

Following sonication with a Branson SONIFIER microtip (three 15 sec blasts with intermittent cooling), the extract was centrifuged successively at 4° C. for 10 minutes at 3000×g, and for 30 minutes at 100,000×g to remove insoluble debris. Glycerol was added to a final concentration of 10% (v/v). After filtering the extract through a 0.2 uM filter unit (Millipore), 500 microliters was loaded onto a SMART SYSTEM FPLC 100 ul MONOQ anion exchange column (Pharmacia).

A linear NaCl gradient was applied (0-500 mM in 3ml @ 100 ul/min) and 100 ul fractions were collected and assayed for PKG enzyme activity. Fractions containing *P. falciparum* PKG activity were pooled and affinity-purified using 8-AET-cGMP-agarose (Biolog, A019). A small scale 0.6 ml column was equilibrated with Buffer G (50 mM HEPES pH 7.4, 10% glycerol, 10 mM sodium fluoride, 0.1 mM sodium orthovanadate, 1 mM EDTA). The enzyme sample was mixed with an equal volume of Buffer G and applied to the column. Immobilized *P. falciparum* PKG was washed with 10 ml of Buffer G and then with 10 ml of Buffer G containing 1 mM GMP. Proteins were eluted with 10 ml of Buffer G containing 15 mM cGMP. The purification of *P. falciparum* PKG was monitored by Western blot analysis using a commercially available antipeptide antisera directed at a conserved PKG peptide (Calbiochem Cat. No. 539729).

(v) PKG Catalytic Assay

Kinase activity was detected using a peptide substrate and [γ-$^{33}$P]-ATP. An aliquot containing the respective enzyme preparations was combined with a reaction mixture (10 μl) whose composition is as follows: 25 mM HEPES pH 7.4, 10 mM MgCl$_2$, 20 mM beta-glycerophosphate, 5 mM beta-mercaptoethanol, 10 μM cGMP, 1 mg/ml BSA, 400 μM Kemptide, 2 μM [γ-$^{33}$P]ATP (0.1 mCi/ml). The reaction was allowed to proceed for 1 hour at room temperature and then terminated with the addition of phosphoric acid to a final concentration of 25 mM. Labeled peptide was captured on P81 filters or on Millipore 96-well plates (MAPH-NOB). In both cases filters were washed with 75 mM phosphoric acid, dried and $^{33}$P-labelled phosphopeptide was detected by liquid scintillation counting.

Summarized below are the $IC_{50}$ values for L-167645 against both native and recombinant expressed *E. maxima* PKG as well as native *P. falciparum* PKG. The native and recombinant *E. maxima* PKG activities are equally sensitive to L-167645. As well, the sensitivity of native *P. falciparum* PKG activity is much the same.

| PKG Enzyme Source | $IC_{50}$ for L-167645 |
|---|---|
| Recombinant *E. maxima* | 4.2 nM |
| Native *E. maxima* | 4.6 nM |
| Native *P. falciparum* | 8.53 nM |

EXAMPLE 2

Efficacy of L-167645 Against *Plasmodium* Species
(i) PFAIV Assay

The PFAIV assay is an in vitro assay designed to identify potential inhibitors of *P. falciparum* by measuring the incorporation of tritiated hypoxanthine into parasitized red blood cells.

PFAIV Assay Protocol

The following method is an adaptation of the method described by Desjardins, R. E. et al, 1979. AAC Vol 16, p710-718:

1. Sixty microliters of a solution of RPMI 1640 media plus gentamycin (1:100 dilution) containing the desired concentration of test compound is added to the wells of a 96-well plate. (For titrations, 120 microliters is added to the top well and the compounds are serially diluted into 60 microliters of media.)

2. Fifty three microliters of parasitized red blood cells is added to the wells. The parasitemia of the culture is approximately 2-3% and the hematocrit is 5%. The red blood cells are diluted in RPMI 1640 media containing 20% human A+ serum and gentamycin.

3. Twelve microliters of RPMI1640 media containing 200 uCi [$^3$H] - hypoxanthine is added to each well.

4. The plates are incubated at 37° C. for 48 hours under reduced $CO_2$ conditions (candle jar). After incubation, the plates are frozen overnight (for safety), then thawed and harvested using a manual 96-well harvester onto UNIFILTER GF/B plates.

5. The plates are counted on a Wallac instrument and % inhibition of parasite growth is determined as compared to control wells containing no compound.

The efficacy of L-167645 against *Plasmodium falciparum* in this in vitro cell culture assay, expressed as the concentration of compound required to inhibit growth by 50% ($IC_{50}$) was determined to be 2.2 ug/ml.

(ii) Efficacy of L-167645 against *Plasmodium* in vivo

Balb C mice were infected intra-peritoneally with $1 \times 10^6$ *P. berghei* parasites in red blood cells. Two hours later twice daily intra-peritoneal treatment began with L-167645 in 10% DMSO. In the experiments described within, five animals were dosed with 75 milligrams compound per kilogram body weight (mpk) and received two treatments for one day. Five additional mice were dosed at 50 mpk and received two treatments daily for five days. Five control mice were dosed with an equivalent volume of 10% DMSO twice daily for 5 days. Parasite burden was measured by counting infected red blood cells as a function of total red blood cells (% parasitemia) and was performed periodically; -parasitemia on day 8 post-infection are tabulated below.

| L-167645 Reduces Parasitemia in Mice Infected with *P. berghei* (% PARASITEMIA 8 DAYS POST-INFECTION) | | | | | |
|---|---|---|---|---|---|
| | Dose | Mouse 1 | Mouse 2 | Mouse 3 | Mouse 4 | Mouse 5 |
| Control | — | 4 | 23 | 20 | >50 | 9 |
| L-167645 | 75 mpk | 3 | 4 | 1 | 1 | Dead |
| L-167645 | 50 mpk | 0 | 0 | 1 | 3 | 1 |

Mouse survival was also monitored during the study and is graphically displayed in FIG. 1.

EXAMPLE 3

Efficacy of L-167,645 Against *Eimeria* Parasites
(i) Efficacy against *E. maxima* in vivo Several studies have been conducted to evaluate the efficacy of L-167545 against *E. maxima* in infected chickens. For efficacy studies against *E. maxima* alone, L-167645 was administered in the feed at doses from 25 to 150 ppm starting on day one. Birds were infected with $3.5 \times 10^3$ *E. maxima* sporalated oocysts on day 2 and medicated feed was continuously available at the respective doses for the duration of the study. The experiment was terminated on day 8, intestines were removed and homogenized and compound efficacy was estimated by performing oocyst counts. In these studies greater than 99% reduction in oocyst counts was achieved at a dose of 125 ppm L-167645.

(ii) In vivo Efficacy of L-167645 Against Mixed-Species Field Isolates of *Eimeria* Containing *E. maxima*

Chicken battery experiments have also been conducted to evaluate L-167645 efficacy against mixed-species field isolates of *Eimeria*. The *Eimeria* cultures were obtained from grower farms in major broiler-producing states. Two of these field isolates, DP-924 and DP-968, contained *E. maxima* parasites. Each treatment group consisted of one pen of three one-week old White Leghorn chickens. Animals were placed on medicated feed at doses of L-167645 ranging from 25 to 150 ppm for the duration of the study. After 48 hrs, birds were infected by oral gavage with a total of $1 \times 10^5$ sporulated oocysts. As depicted in the table below, the 125 ppm level of L-167645 resulted in good weight gain and control of oocyst production.

| Efficacy of L-167645 in Chickens Infected with Mixed-Species Field Isolates of *Eimeria* | | |
|---|---|---|
| | Culture ID | |
| | DP-924 | DP-968 |
| Origin of Field Isolate | N. Carolina | DELMARVA |
| Component Species | *E. maxima* | *E. maxima* |
| | *E. acervulina* | *E. acervulina* |
| | *E. mitis* | *E. mitis* |
| | | *E. tenella* |
| % Reduction in Oocyst Counts | 97 | 86 |
| Relative % Weight Gain | 108 | 94 |

While the invention has been described in detail with reference to certain preferred embodiments thereof, it will be understood that modifications and variations are within the spirit and scope of that which is described and claimed.

Summary of Sequence Listing:

SEQ ID NO:1 is the nucleotide sequence encoding the *Eimeria maxima* PKG.

SEQ ID NO:2 is the deduced amino acid of the gene product of SEQ ID NO;1.

SEQ ID NO:3 is the nucleotide sequence encoding a *Plasmodium falciparum* PKG.

SEQ ID NO:4 is the deduced amino acid of the gene product of SEQ ID NO:3

What is claimed is:

1. An isolated nucleic acid molecule, comprising a sequence of nucleotides that encode an *Eimeria maxima* cGMP dependent protein kinase (PKG), wherein the sequence of nucleotides is selected from the group consisting of:

(a) a sequence of nucleotides that encodes an *Eimeria maxima* cGMP dependent protein kinase (PKG) comprising the nucleotide sequence of SEQ ID NO: 1; and (b) a sequence of nucleotides that encodes an *Eimeria maxima* cGMP dependent protein kinase (PKG) comprising the amino acid sequence of SEQ ID NO:2.

2. A recombinant nucleic acid molecule comprising a nucleic acid sequence according to claim 1 operatively linked to expression control sequences enabling expression of said nucleic acid sequence.

3. An isolated host cell transformed with the recombinant nucleic acid molecule according to claim 2.

4. An immunogenic composition, comprising a recombinant nucleic acid molecule according to claim 2, together with a pharmaceutically acceptable carrier.

5. An immunogenic composition, comprising the nucleic acid molecule of claim 1, together with a pharmaceutically acceptable carrier.

6. An isolated nucleic acid molecule that encodes an *Eimeria maxima* cGMP dependent protein kinase (PKG) comprising the amino acid sequence of SEQ ID NO:2.

7. The isolated nucleic acid molecule of claim 6 wherein the nucleic acid molecule comprises the nucleotide sequence of SEQ ID NO: 1.

* * * * *

```
                       SEQUENCE LISTING

<160> NUMBER OF SEQ ID NOS: 4

<210> SEQ ID NO 1
<211> LENGTH: 3430
<212> TYPE: DNA
<213> ORGANISM: Prokaryote

<400> SEQUENCE: 1
atgggcgcat gcagctctaa ggcgcagcaa cagacacgcg atccggagcc acgagagcag      60
cagcctgcgc tcgagcccaa aacctccgaa ccctgcggcc cttctgacgc cgccgcacct     120
gtcgaggcgg ttaggaagat gtcgggttcg agcgccacgg cgcctaaagg tgaaatgcct     180
acagccagta caggtactcc tgagcagcag cagcagcagc aggagcagca gcagcagcag     240
cagcagcagc tagagcggca gcaacagcag cagcaggagc agcaacagca ccaggagcag     300
cagcagcagc agcaggagca gcaggaacag cagcagcagg acaggaaaac ctcacagccg     360
cagcaaaacg atgatgcagc tgcaccaccc aagccggggg gtgagcggaa ggctcagaag     420
gcgatcatgc agcaggatga tacacaagca gaggatgcta gacttttgaa ccacctggag     480
aagcgggaga agacggacag tgatctgtct ttaattcgtt cttcccttcc gggcaactta     540
gtttgctctt ctctaaatga ttcggaggtt gaggcacttg cgaatgccgt ccaattcttc     600
acctttgcaa agggagatat cgtcacaaaa caaggagaaa acggcagtta cttcttcatt     660
gttcacagtg gagagttcga ggtgatagtg aacgagaagg tggttaacaa gatagtgcag     720
ggccaagcct tcggagaaat ttctttaatt cacaattctg cgaggactgc aacaattaaa     780
accctcagcg accaggccgc cctgtggggc gtgcagagac aagttttcag ggagacgctg     840
aagcagctga gcagcagaaa cttcgcagag aatcggcagt ttttggcctc agttgaattt     900
ttccaaatgc taacggaggc gcaaaagaat gtgataacta acgcgctagt ggttcaatct     960
ttcaagccgg ggcagccaat tgtcaaggaa ggggaaaaag gagacatttt gtatatcata    1020
aagagcggga aggcgcgagt ctccattaaa ggcaaagatg ttcggctttt gcagaaggga    1080
gactactttg gggagagggc gctgctgtac gacgagcctc gcagtgccac aattacggca    1140
gaagaggaga caatttgtgt ttctattgga agggatctcc ttgatagagt tcttggtaac    1200
ctccaacatg tcctcttccg caatattatg ctcgaagctc tgcaacaaag caaggtgttt    1260
gcgtcctttc cgacggagca actgagccga ttgattggct cggtggttgt aaaggattat    1320
ccggagaatt atctcatact cgacagagag aacaggacta agcttcggc ttcgccgctg    1380 ttctcggcac agggcgttcg cttttctctt gtattagaag gggaagtttc ggtctacgct    1440
tacagggagg cccccagcgc cagcagcagc ggaggtggca gcagcagcgg agagccgcgg    1500
atggagctga atttggttga tacacttaaa aggggtcagg ccttcggcga tgaatatgtg    1560
ttgtctccta ataagccctt cgcccactgc gtgcgcagca atgggcccgc gaagctggct    1620
ttgcttactg cgacgcctt gacggcgact ttgggcggcc aagacataga cgagacttta     1680
gactacaaca acaaattggc cattactaaa aagatgtata ttttccgata cctttctgag    1740
```

-continued

```
caacagacgc aaaccctcat tcgcgccttc aaaaccgttc ggtacaccca aggggaggca   1800
attatccgcg agggagagat cggttcgcgt ttcttcatta ttaaacttgg agaggtggcg   1860
attctgaagg ggggccgtcg tgtacgtact ttgggccgcc atgattactt tgggagaga    1920
gctttgctgc atgacgagag gcgaagtgca actgttgcag caaatagccc tgaggttgac   1980
ttgtgggtag tggataaaga tgtcttccta caaattgtta agggacccat gctaacccac   2040
ttggaagaac gtattcggat gcaagacacc aaagttgaat tcaaagactt gcaggtcgtc   2100
cgcgtcgtcg aagaggcac cttcgggacg gtgaagttgg tgcagcacat tcccacgaag    2160
attcgttatg cgttaaagtg cgtctctcga agagcgtcg tcgctttaaa ccagcaagat    2220
catatccgcc tagagaggga gatcatggcc gaaaacgacc atcccttcat catccgactc   2280
gtgcggacgt tccgggacaa ggactttctc tacttttga ccgagttggt tacgggagga    2340
gaattgtatg atgccatcag aaagctaggc cttctgggga ggtaccaagc acagttttac   2400
ttggcttcca ttgtcctggc tattgaatat ctccatgaaa gaaatatcgc ctacagagat   2460
ctcaagccgg agaacatttt gctggactcg caaggttatg tgaaactgat tgactttggg   2520
tgtgcaaaga aaatgcaagg aagggcctac actttagtgg gaactccaca ttacatggct   2580
ccagaagtca ttctaggcaa aggatataca ctgacagcag acacttgggc ctttggggtt   2640
tgtctttatg aatttatgtg cggccctctt ccctttggaa atgacgcgga agatcagcta   2700
gaaatcttca gggatatcct tgcagggaag ctgatgttcc ctcactacgt gacggatcaa   2760
gatgcaataa acctaatgaa gcgactgctg tgtcgtctac cggaagttcg cattggttgt   2820
tctattaacg gatacaaaga cataaaggag catgcttttct tctcggattt cgattgggat   2880
cgcctagctg ggagagattt atcccctcct cttcttccta aaggcgaaac atacgctgaa   2940
gacgcagagg agggagggct ggagatagaa gaagacgaag gaattgagct ggaagatgaa   3000
tatgattggg ataaggactt ctaaaaccta aagcccctaa accctagacg tgtctctttgc  3060
agtgttccct gctgcacaag tgtacagcct atcgaccttc gtctggtgct ctgaccacag   3120
cagatgcagc agcagcagca gatgcatatg cagcagatgc agcggcagca gcagatgcaa   3180
agcgggatac ttacacgtag cggcagcgct gtctcggcac atcgtgctgt tgtttcagca   3240
gcaggaacag cagcagatgc agcaggtgca gcacatgcag atgcagcagc agcctttggt   3300
gttgttgttg gttgcttctg agtggtttat ctctctgttg ttatgtttac ttctttagtt   3360
cttcgcatgc ttgtgctctc acaaacgcta aaccctaaac cctcattcag agaaaaaaaa   3420
aaaaaaaaaa                                                         3430
```

<210> SEQ ID NO 2
<211> LENGTH: 1007
<212> TYPE: PRT
<213> ORGANISM: Prokaryote

<400> SEQUENCE: 2

Met Gly Ala Cys Ser Ser Lys Ala Gln Gln Gln Thr Arg Asp Pro Glu
 1               5                  10                  15

Pro Arg Glu Gln Gln Pro Ala Leu Glu Pro Lys Thr Ser Glu Pro Cys
            20                  25                  30

Gly Pro Ser Asp Ala Ala Ala Pro Val Glu Ala Val Arg Lys Met Ser
        35                  40                  45

Gly Ser Ser Ala Thr Ala Pro Lys Gly Glu Met Pro Thr Ala Ser Thr
    50                  55                  60

Gly Thr Pro Glu Gln Gln Gln Gln Gln Gln Glu Gln Gln Gln Gln Gln

-continued

```
                65                  70                  75                  80
Gln Gln Gln Leu Glu Arg Gln Gln Gln Gln Glu Gln Gln Gln
                    85                  90                  95
His Gln Glu Gln Gln Gln Gln Gln Glu Gln Glu Gln Gln Gln
                    100                 105                 110
Gln Asp Arg Lys Thr Ser Gln Pro Gln Gln Asn Asp Ala Ala Ala
                115                 120                 125
Pro Pro Lys Pro Gly Gly Glu Arg Lys Ala Gln Lys Ala Ile Met Gln
    130                 135                 140
Gln Asp Asp Thr Gln Ala Glu Asp Ala Arg Leu Leu Asn His Leu Glu
145                 150                 155                 160
Lys Arg Glu Lys Thr Asp Ser Asp Leu Ser Leu Ile Arg Ser Ser Leu
                165                 170                 175
Ser Gly Asn Leu Val Cys Ser Ser Leu Asn Asp Ser Glu Val Glu Ala
                180                 185                 190
Leu Ala Asn Ala Val Gln Phe Phe Thr Phe Ala Lys Gly Asp Ile Val
                195                 200                 205
Thr Lys Gln Gly Glu Asn Gly Ser Tyr Phe Phe Ile Val His Ser Gly
                210                 215                 220
Glu Phe Glu Val Ile Val Asn Glu Lys Val Val Asn Lys Ile Val Gln
225                 230                 235                 240
Gly Gln Ala Phe Gly Glu Ile Ser Leu Ile His Asn Ser Ala Arg Thr
                245                 250                 255
Ala Thr Ile Lys Thr Leu Ser Asp Gln Ala Ala Leu Trp Gly Val Gln
                260                 265                 270
Arg Gln Val Phe Arg Glu Thr Leu Lys Gln Leu Ser Ser Arg Asn Phe
                275                 280                 285
Ala Glu Asn Arg Gln Phe Leu Ala Ser Val Glu Phe Phe Gln Met Leu
                290                 295                 300
Thr Glu Ala Gln Lys Asn Val Ile Thr Asn Ala Leu Val Val Gln Ser
305                 310                 315                 320
Phe Lys Pro Gly Gln Pro Ile Val Lys Glu Gly Glu Lys Gly Asp Ile
                325                 330                 335
Leu Tyr Ile Ile Lys Ser Gly Lys Ala Arg Val Ser Ile Lys Gly Lys
                340                 345                 350
Asp Val Arg Leu Leu Gln Lys Gly Asp Tyr Phe Gly Glu Arg Ala Leu
                355                 360                 365
Leu Tyr Asp Glu Pro Arg Ser Ala Thr Ile Thr Ala Glu Glu Thr
                370                 375                 380
Ile Cys Val Ser Ile Gly Arg Asp Leu Leu Asp Arg Val Leu Gly Asn
385                 390                 395                 400
Leu Gln His Val Leu Phe Arg Asn Ile Met Leu Glu Ala Leu Gln Gln
                405                 410                 415
Ser Lys Val Phe Ala Ser Phe Pro Thr Glu Gln Leu Ser Arg Leu Ile
                420                 425                 430
Gly Ser Val Val Val Lys Asp Tyr Pro Glu Asn Tyr Leu Ile Leu Asp
                435                 440                 445
Arg Glu Asn Arg Thr Lys Ala Ser Ala Ser Pro Leu Phe Ser Ala Gln
                450                 455                 460
Gly Val Arg Phe Phe Phe Val Leu Glu Gly Glu Val Ser Val Tyr Ala
465                 470                 475                 480
Tyr Arg Glu Ala Pro Ser Ala Ser Ser Ser Gly Gly Gly Ser Ser Ser
                485                 490                 495
```

```
Gly Glu Pro Arg Met Glu Leu His Leu Val Asp Thr Leu Lys Arg Gly
            500                 505                 510

Gln Ala Phe Gly Asp Glu Tyr Val Leu Ser Pro Asn Lys Pro Phe Ala
        515                 520                 525

His Cys Val Arg Ser Asn Gly Pro Ala Lys Leu Ala Leu Leu Thr Ala
    530                 535                 540

Ser Ala Leu Thr Ala Thr Leu Gly Gly Gln Asp Ile Asp Glu Thr Leu
545                 550                 555                 560

Asp Tyr Asn Asn Lys Leu Ala Ile Thr Lys Lys Met Tyr Ile Phe Arg
                565                 570                 575

Tyr Leu Ser Glu Gln Gln Thr Gln Thr Leu Ile Arg Ala Phe Lys Thr
            580                 585                 590

Val Arg Tyr Thr Gln Gly Glu Ala Ile Ile Arg Glu Gly Glu Ile Gly
        595                 600                 605

Ser Arg Phe Phe Ile Ile Lys Leu Gly Glu Val Ala Ile Leu Lys Gly
    610                 615                 620

Gly Arg Arg Val Arg Thr Leu Gly Arg His Asp Tyr Phe Gly Glu Arg
625                 630                 635                 640

Ala Leu Leu His Asp Glu Arg Arg Ser Ala Thr Val Ala Ala Asn Ser
                645                 650                 655

Pro Glu Val Asp Leu Trp Val Val Asp Lys Val Phe Leu Gln Ile
            660                 665                 670

Val Lys Gly Pro Met Leu Thr His Leu Glu Glu Arg Ile Arg Met Gln
        675                 680                 685

Asp Thr Lys Val Glu Phe Lys Asp Leu Gln Val Val Arg Val Val Gly
    690                 695                 700

Arg Gly Thr Phe Gly Thr Val Lys Leu Val Gln His Ile Pro Thr Lys
705                 710                 715                 720

Ile Arg Tyr Ala Leu Lys Cys Val Ser Arg Lys Ser Val Val Ala Leu
                725                 730                 735

Asn Gln Gln Asp His Ile Arg Leu Glu Arg Glu Ile Met Ala Glu Asn
            740                 745                 750

Asp His Pro Phe Ile Ile Arg Leu Val Arg Thr Phe Arg Asp Lys Asp
        755                 760                 765

Phe Leu Tyr Phe Leu Thr Glu Leu Val Thr Gly Gly Glu Leu Tyr Asp
    770                 775                 780

Ala Ile Arg Lys Leu Gly Leu Leu Gly Arg Tyr Gln Ala Gln Phe Tyr
785                 790                 795                 800

Leu Ala Ser Ile Val Leu Ala Ile Glu Tyr Leu His Glu Arg Asn Ile
                805                 810                 815

Ala Tyr Arg Asp Leu Lys Pro Glu Asn Ile Leu Leu Asp Ser Gln Gly
            820                 825                 830

Tyr Val Lys Leu Ile Asp Phe Gly Cys Ala Lys Lys Met Gln Gly Arg
        835                 840                 845

Ala Tyr Thr Leu Val Gly Thr Pro His Tyr Met Ala Pro Glu Val Ile
    850                 855                 860

Leu Gly Lys Gly Tyr Thr Leu Thr Ala Asp Thr Trp Ala Phe Gly Val
865                 870                 875                 880

Cys Leu Tyr Glu Phe Met Cys Gly Pro Leu Pro Phe Gly Asn Asp Ala
                885                 890                 895

Glu Asp Gln Leu Glu Ile Phe Arg Asp Ile Leu Ala Gly Lys Leu Met
            900                 905                 910
```

```
Phe Pro His Tyr Val Thr Asp Gln Asp Ala Ile Asn Leu Met Lys Arg
        915                 920                 925

Leu Leu Cys Arg Leu Pro Glu Val Arg Ile Gly Cys Ser Ile Asn Gly
        930                 935                 940

Tyr Lys Asp Ile Lys Glu His Ala Phe Phe Ser Asp Phe Asp Trp Asp
945                 950                 955                 960

Arg Leu Ala Gly Arg Asp Leu Ser Pro Pro Leu Leu Pro Lys Gly Glu
                965                 970                 975

Thr Tyr Ala Glu Asp Ala Glu Glu Gly Gly Leu Glu Ile Glu Glu Asp
            980                 985                 990

Glu Gly Ile Glu Leu Glu Asp Glu Tyr Asp Trp Asp Lys Asp Phe
        995                 1000                1005

<210> SEQ ID NO 3
<211> LENGTH: 3197
<212> TYPE: DNA
<213> ORGANISM: Prokaryote

<400> SEQUENCE: 3
```

| | | | | | |
|---|---|---|---|---|---|
| actttttttt | tttttttttt | ttaatttgta | tacacaaaga | tttagagaga | aattaagtgt | 60 |
| atataaaata | tataatagat | aataaaaaaa | aaaaaaaaaa | atggaagaag | atgataatct | 120 |
| aaaaaaaggg | aatgaaagaa | ataaaagaaa | ggctatattt | tcaaatgatg | attttacagg | 180 |
| agaagatagt | ttaatggagg | atcatttaga | acttcgggaa | aagctttcag | aagatattga | 240 |
| tatgataaag | acttccttaa | aaaataatct | agtttgtagt | acattaaacg | ataatgaaat | 300 |
| attgactctg | tctaattata | tgcaattctt | tgttttaaaa | agtggaaatt | tagtaataaa | 360 |
| acaaggggaa | aaagggtcat | actttttcat | tattaatagt | ggcaaatttg | acgtttatgt | 420 |
| aaatgataaa | aaagtaaaga | ctatgggaaa | aggtagttct | ttcggtgaag | ctgctttaat | 480 |
| tcataatacc | caaagaagtg | caactattat | tgcagaaact | gatggaactc | tatggggagt | 540 |
| tcaaagaagt | acatttagag | ctaccctaaa | acaattatct | aatagaaatt | ttaacgaaaa | 600 |
| cagaacattt | atcgattccg | tttcagtttt | tgatatgtta | actgaagcac | aaaaaaacat | 660 |
| gattactaat | gcttgtgtaa | tacaaaactt | taaatctggt | gaaaccattg | ttaaacaagg | 720 |
| agattatgga | gatgtcttat | acatttttgaa | agaaggaaag | gctacagtat | atattaacga | 780 |
| tgaagagata | agggttttag | agaaaggttc | ctattttggg | gaaagagctc | tactgtatga | 840 |
| tgaaccaaga | agtgcaacaa | tcattgcaaa | agaaccaacc | gcttgtgcat | ccatttgtag | 900 |
| gaaattatta | aatattgttc | taggaaactt | acaagtagtt | ttatttcgta | atattatgac | 960 |
| tgaagcttta | caacagagtg | aaattttttaa | acaatttagt | ggggatcaat | taaacgattt | 1020 |
| agcagatacc | gccattgttc | gagattatcc | agctaattat | aatatattac | ataaggataa | 1080 |
| ggtaaaatcc | gttaaatata | ttattgtatt | ggaaggtaaa | gtagaattat | tcttgatga | 1140 |
| tacttctatt | ggtatattat | ccagaggaat | gtctttggga | gatcaaatg | tattaaatca | 1200 |
| gaaacaacca | tttaagcata | ctattaaatc | attagaagtt | tgtaaaatcg | cattaataac | 1260 |
| ggaaacttgt | ttagctgatt | gtctaggaaa | taataatatt | gatgcatcta | ttgattataa | 1320 |
| taataaaaaa | agtattataa | agaaaatgta | tatctttaga | tacttaactg | ataaacaatg | 1380 |
| taatttatta | attgaagctt | ttagaaccac | aagatatgaa | gaaggtgatt | atataataca | 1440 |
| agaaggagaa | gtaggatcta | gatttatat | aataaaaaat | ggagaagtag | aaatagtaaa | 1500 |
| aaataaaaaa | aggttacgta | ccttaggaaa | gaatgattac | tttggtgaaa | gagctttatt | 1560 |
| atatgatgaa | ccaagaacag | cttctgttat | aagtaaagta | aataatgttg | aatgttggtt | 1620 |

```
tgttgataaa agtgtgtttt tacaaattat acaaggacct atgttagcac atttggaaga      1680
aagaataaaa atgcaagata ctaaagtaga atggatgaa ctagaaacag aacgaattat       1740
tggaagaggt actttcggaa cagttaaatt agttcatcat aaaccaacaa aaataagata     1800
tgctttaaaa tgtgttagta aagaagtat tattaattta aatcaacaaa acaatataaa      1860
attagaaaga gaaataacag cagaaaatga tcatccattt attataagat tagtaagaac     1920
atttaaagat tctaaatatt tctattttct aacagaatta gtaacaggtg gagaattata    1980
tgatgctatt agaaaattag gtttattatc taaatcacaa gctcaatttt atttaggttc     2040
tatcatttta gctattgaat atttacatga aagaaatatt gtatatagag atttaaaacc    2100
agaaaacatt ttattagata acaaggtta tgtaaaacta atcgattttg gttgtgccaa     2160
aaaggtacaa ggtagagctt atacattagt aggtacacct cattatatgg cacctgaggt    2220
tattttagga aaaggttatg gatgtactgt tgacatatgg gcattgggaa tatgcctata    2280
tgaatttata tgtggtccat taccatttgg taatgatgaa gaagatcaat tagaaatttt    2340
ccgtgatata ttaaccggcc aacttacatt tccagattat gtaacagaca cagatagcat    2400
aaatttgatg aaaagacttc tatgtagatt acctcaagga agaattggtt gttcaataaa   2460
tggcttcaaa gacataaagg atcacccatt tttctcaaac tttaattggg ataaattggc    2520
tggtcgtttg cttgatccgc ctttagtatc aaaaagtgaa acttatgcag aagatattga    2580
tattaaacaa atagaggagg aggatgctga ggatgatgag gaaccattga acgatgaaga   2640
caactgggac atagattttt aaataaataa ataaataaaa tatatatata tatgtagaga   2700
tatatatata cttaattagg gcgatatgat aattgaaagg attattattt tttaattttt    2760
ttagtatatt tttagaaatc atatatattc ataatatat atttgttcca tcatatatat     2820
tatatatata tatatattat atatatatat aataattata aattttgaa aaatgttatt     2880 tttattatta ataatttttt tttttttttc atttgtttgt acaatataat gaatttatat    2940
cttgcggtgt ttttttttat tctctccttt tttatattat atttattt attttattct    3000 ttttcttttt tttttttttct tttttttttt ttgtttgttt ttaattttac aaatatttt   3060 aaataaaaat tcaaatggtt ctaaattttt ttaataaata aaaaaaaaa aaaaaaaaa    3120 aaaaaaaaaa aaaaaaaaa aaaaaaaaa aaaaaaaaa aaaaaaaaa aaaaaaaaa        3180 aaaaaaaaaa aaaaaaa                                                    3197
```

<210> SEQ ID NO 4
<211> LENGTH: 854
<212> TYPE: PRT
<213> ORGANISM: Prokaryote

<400> SEQUENCE: 4

```
Met Glu Glu Asp Asp Asn Leu Lys Lys Gly Asn Glu Arg Asn Lys Lys
  1               5                  10                  15

Lys Ala Ile Phe Ser Asn Asp Asp Phe Thr Gly Glu Asp Ser Leu Met
             20                  25                  30

Glu Asp His Leu Glu Leu Arg Glu Lys Leu Ser Glu Asp Ile Asp Met
         35                  40                  45

Ile Lys Thr Ser Leu Lys Asn Asn Leu Val Cys Ser Thr Leu Asn Asp
     50                  55                  60

Asn Glu Ile Leu Thr Leu Ser Asn Tyr Met Gln Phe Phe Val Phe Lys
 65                  70                  75                  80

Ser Gly Asn Leu Val Ile Lys Gln Gly Glu Lys Gly Gly Ser Tyr Phe
```

-continued

```
                85                  90                  95
Phe Ile Ile Asn Ser Gly Lys Phe Asp Val Tyr Val Asn Asp Lys Lys
            100                 105                 110

Val Lys Thr Met Gly Lys Gly Ser Ser Phe Gly Glu Ala Ala Leu Ile
            115                 120                 125

His Asn Thr Gln Arg Ser Ala Thr Ile Ile Ala Glu Thr Asp Gly Thr
            130                 135                 140

Leu Trp Gly Val Gln Arg Ser Thr Phe Arg Ala Thr Leu Lys Gln Leu
145                 150                 155                 160

Ser Asn Arg Asn Phe Asn Glu Asn Arg Thr Phe Ile Asp Ser Val Ser
                165                 170                 175

Val Phe Asp Met Leu Thr Glu Ala Gln Lys Asn Met Ile Thr Asn Ala
                180                 185                 190

Cys Val Ile Gln Asn Phe Lys Ser Gly Glu Thr Ile Val Lys Gln Gly
                195                 200                 205

Asp Tyr Gly Asp Val Leu Tyr Ile Leu Lys Glu Gly Lys Ala Thr Val
            210                 215                 220

Tyr Ile Asn Asp Glu Glu Ile Arg Val Leu Lys Gly Ser Tyr Phe
225                 230                 235                 240

Gly Glu Arg Ala Leu Leu Tyr Asp Glu Pro Arg Ser Ala Thr Ile Ile
                245                 250                 255

Ala Lys Glu Pro Thr Ala Cys Ala Ser Ile Cys Arg Lys Leu Leu Asn
                260                 265                 270

Ile Val Leu Gly Asn Leu Gln Val Val Leu Phe Arg Asn Ile Met Thr
            275                 280                 285

Glu Ala Leu His Gln Ser Glu Ile Phe Asn Gln Phe Ser Gly Asp Gln
            290                 295                 300

Leu Asn Asp Leu Ala Asp Thr Ala Ile Val Arg Asp Tyr Pro Ala Asn
305                 310                 315                 320

Tyr Asn Ile Leu His Lys Asp Lys Val Lys Ser Val Lys Tyr Ile Ile
                325                 330                 335

Val Leu Glu Gly Lys Val Glu Leu Phe Leu Asp Asp Thr Ser Ile Gly
            340                 345                 350

Ile Leu Ser Arg Gly Met Ser Phe Gly Asp Gln Tyr Val Leu Asn Gln
            355                 360                 365

Lys Gln Pro Phe Lys His Thr Ile Lys Ser Leu Glu Val Cys Lys Ile
            370                 375                 380

Ala Leu Ile Thr Glu Thr Cys Leu Ala Asp Cys Leu Gly Asn Asn Asn
385                 390                 395                 400

Ile Asp Ala Ser Ile Asp Tyr Asn Asn Lys Ser Ile Ile Lys Lys
                405                 410                 415

Met Tyr Ile Phe Arg Tyr Leu Thr Asp Lys Gln Cys Asn Leu Leu Ile
            420                 425                 430

Glu Ala Phe Arg Thr Thr Arg Tyr Glu Glu Gly Asp Tyr Ile Ile Gln
            435                 440                 445

Glu Gly Glu Val Gly Ser Arg Phe Tyr Ile Ile Lys Asn Gly Glu Val
            450                 455                 460

Glu Ile Val Lys Asn Lys Lys Arg Leu Arg Thr Leu Gly Lys Asn Asp
465                 470                 475                 480

Tyr Phe Gly Glu Arg Ala Leu Leu Tyr Asp Glu Pro Arg Thr Ala Ser
                485                 490                 495

Val Ile Ser Lys Val Asn Asn Val Glu Cys Trp Phe Val Asp Lys Ser
            500                 505                 510
```

-continued

```
Val Phe Leu Gln Ile Ile Gln Gly Pro Met Leu Ala His Leu Glu Glu
        515                 520                 525

Arg Ile Lys Met Gln Asp Thr Lys Val Glu Met Asp Glu Leu Glu Thr
        530                 535                 540

Glu Arg Ile Ile Gly Arg Gly Thr Phe Gly Thr Val Lys Leu Val His
545                 550                 555                 560

His Lys Pro Thr Lys Ile Arg Tyr Ala Leu Lys Cys Val Ser Lys Arg
                565                 570                 575

Ser Ile Ile Asn Leu Asn Gln Gln Asn Asn Ile Lys Leu Glu Arg Glu
            580                 585                 590

Ile Thr Ala Glu Asn Asp His Pro Phe Ile Ile Arg Leu Val Arg Thr
        595                 600                 605

Phe Lys Asp Ser Lys Tyr Phe Tyr Phe Leu Thr Glu Leu Val Thr Gly
        610                 615                 620

Gly Glu Leu Tyr Asp Ala Ile Arg Lys Leu Gly Leu Leu Ser Lys Ser
625                 630                 635                 640

Gln Ala Gln Phe Tyr Leu Gly Ser Ile Ile Leu Ala Ile Glu Tyr Leu
                645                 650                 655

His Glu Arg Asn Ile Val Tyr Arg Asp Leu Lys Pro Glu Asn Ile Leu
            660                 665                 670

Leu Asp Lys Gln Gly Tyr Val Lys Leu Ile Asp Phe Gly Cys Ala Lys
        675                 680                 685

Lys Val Gln Gly Arg Ala Tyr Thr Leu Val Gly Thr Pro His Tyr Met
        690                 695                 700

Ala Pro Glu Val Ile Leu Gly Lys Gly Tyr Gly Cys Thr Val Asp Ile
705                 710                 715                 720

Trp Ala Leu Gly Ile Cys Leu Tyr Glu Phe Ile Cys Gly Pro Leu Pro
                725                 730                 735

Phe Gly Asn Asp Glu Glu Asp Gln Leu Glu Ile Phe Arg Asp Ile Leu
            740                 745                 750

Thr Gly Gln Leu Thr Phe Pro Asp Tyr Val Thr Asp Thr Asp Ser Ile
        755                 760                 765

Asn Leu Met Lys Arg Leu Leu Cys Arg Leu Pro Gln Gly Arg Ile Gly
        770                 775                 780

Cys Ser Ile Asn Gly Phe Lys Asp Ile Lys Asp His Pro Phe Phe Ser
785                 790                 795                 800

Asn Phe Asn Trp Asp Lys Leu Ala Gly Arg Leu Leu Asp Pro Pro Leu
                805                 810                 815

Val Ser Lys Ser Glu Thr Tyr Ala Glu Asp Ile Asp Ile Lys Gln Ile
            820                 825                 830

Glu Glu Glu Asp Ala Glu Asp Asp Glu Glu Pro Leu Asn Asp Glu Asp
        835                 840                 845

Asn Trp Asp Ile Asp Phe
        850
```